United States Patent
Brown et al.

(10) Patent No.: US 7,031,771 B2
(45) Date of Patent: Apr. 18, 2006

(54) DUAL CHAMBER METHOD AND APPARATUS FOR DIAGNOSIS AND TREATMENT OF ARRHYTHMIAS

(75) Inventors: Mark L. Brown, North Oaks, MN (US); Jeffrey M. Gillberg, Coon Rapids, MN (US); Robert W. Stadler, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 503 days.

(21) Appl. No.: 10/308,281

(22) Filed: Dec. 3, 2002

(65) Prior Publication Data

US 2003/0144700 A1 Jul. 31, 2003

Related U.S. Application Data

(60) Provisional application No. 60/337,111, filed on Dec. 3, 2001.

(51) Int. Cl.
*A61N 1/362* (2006.01)
(52) U.S. Cl. .................. 607/14; 607/25; 600/518
(58) Field of Classification Search ................ 607/14, 607/25
See application file for complete search history.

(56) References Cited

U.S. PATENT DOCUMENTS

| | | | |
|---|---|---|---|
| 4,316,472 A | 2/1982 | Mirowski et al. | |
| 4,375,817 A | 3/1983 | Engle et al. | |
| 4,384,585 A | 5/1983 | Zipes | |
| 4,577,633 A | 3/1986 | Berkovits et al. | |
| 4,587,970 A | 5/1986 | Holley et al. | |
| 4,726,380 A | 2/1988 | Vollmann et al. | |
| 4,727,877 A | 3/1988 | Kallok | |
| 4,830,006 A | 5/1989 | Haluska et al. | |
| 4,880,005 A | 11/1989 | Pless et al. | |
| 4,949,719 A | 8/1990 | Pless et al. | |
| 5,117,824 A | 6/1992 | Keimel et al. | |
| 5,141,581 A | 8/1992 | Markham | |
| 5,163,427 A | 11/1992 | Keimel | |
| 5,188,105 A | 2/1993 | Keimel | |
| 5,312,441 A | 5/1994 | Mader et al. | |
| 5,330,508 A | 7/1994 | Gunderson | |
| 5,342,402 A | 8/1994 | Olson et al. | |
| 5,439,483 A * | 8/1995 | Duong-Van | 607/5 |
| 5,545,186 A | 8/1996 | Olson et al. | |
| 5,755,736 A | 5/1998 | Gillberg et al. | |

(Continued)

FOREIGN PATENT DOCUMENTS

EP 0469817 A2 7/1991

(Continued)

OTHER PUBLICATIONS

Koyrakh, et al., "Wavelet Transform Based Algorithms for EGM Morphology Discrimination for Implantable ICDs", *Computers in Cardiology*, 1999; 26:343-346.

(Continued)

*Primary Examiner*—Robert E. Pezzuto
*Assistant Examiner*—Tammie K. Heller
(74) *Attorney, Agent, or Firm*—Michael C. Soldner; Girma Wolde-Michael

(57) ABSTRACT

A method and apparatus are provided for improving the detection of certain cardiac rhythms by combining dual chamber interval-related detection methods with electrogram morphology analysis. A prioritized set of rules are defined wherein each rule is directed at identifying a particular arrhythmia or type of arrhythmia. Each rule includes clauses that may be related to sensed event intervals and interval patterns and at least one rule includes at least one clause relating to the EGM morphology.

18 Claims, 11 Drawing Sheets

U.S. PATENT DOCUMENTS

| | | | |
|---|---|---|---|
| 5,978,700 A * | 11/1999 | Nigam | 600/518 |
| 5,991,656 A | 11/1999 | Olson et al. | |
| 6,259,947 B1 | 7/2001 | Olson et al. | |
| 6,272,377 B1 | 8/2001 | Sweeney et al. | 600/515 |
| 6,393,316 B1 | 5/2002 | Gillberg et al. | |
| 6,671,548 B1 * | 12/2003 | Mouchawar et al. | 607/14 |
| 2002/0177878 A1 * | 11/2002 | Poore et al. | 607/9 |

FOREIGN PATENT DOCUMENTS

| | | |
|---|---|---|
| EP | 0993842 A1 | 4/2000 |
| EP | 1112758 A2 | 7/2001 |
| WO | WO 92/18198 | 10/1992 |
| WO | WO 00/69517 | 11/2000 |

OTHER PUBLICATIONS

Stroobandt, Roland, "Morphology Discrimination of Ventricular Tachycardia from Supraventricular Tachycardia by Implantable Cardioverter Defibrillators: Are Implantable Carioverter Defibrillators Really Starting to Look at Arrhythmias with the Eyes of a Cardioiogist", *Journal of Cardiovascular Electrophysiology*, vol 13, No. 5, May 2002, 442-443.

Brown, M.L., "Improved Discrimination of VT from SVT in Dual-Chamber ICDs by Combined Analysis of Dual-Chamber Intervals and Ventricular EGM Morphology".

"Discrimination of VT/VF from SVT Using Dual Chamber Intervals and Ventricular Morphology".

* cited by examiner

DUAL CHAMBER METHOD AND APPARATUS FOR DIAGNOSIS AND TREATMENT OF ARRHYTHMIAS

RELATED APPLICATION

This application claims priority and other benefits from U.S. Provisional Patent Application Ser. No. 60/337,111, filed Dec. 3, 2001, entitled "DUAL CHAMBER METHOD AND APPARATUS FOR DIAGNOSIS AND TREATMENT OF ARRHYTHMIAS".

FIELD OF THE INVENTION

The present invention relates generally to implantable medical devices, and more particularly, the present invention relates to the detection and treatment of cardiac arrhythmias using combined interval-based and morphology-based methodologies for detecting arrhythmias.

BACKGROUND OF THE INVENTION

Implantable medical devices are available for treating cardiac arrhythmias by delivering electrical shock therapy for cardioverting or defibrillating the heart in addition to cardiac pacing. Such a device, commonly known as an implantable cardioverter defibrillator or "ICD", senses a patient's heart rhythm and classifies the rhythm according to an arrhythmia detection scheme in order to detect episodes of tachycardia or fibrillation. Single chamber devices are available for treating either atrial arrhythmias or ventricular arrhythmias, and dual chamber devices are available for treating both atrial and ventricular arrhythmias. Arrhythmias detected may include ventricular tachycardia (VT), fast ventricular tachycardia (FVT), ventricular fibrillation (VF), atrial tachycardia (AT) and atrial fibrillation (AT).

Upon detecting an arrhythmia, the ICD delivers an appropriate therapy. Cardiac pacing is delivered in response to the absence of sensed intrinsic depolarizations, referred to as P-waves in the atrium and R-waves in the ventricle. In response to tachycardia detection, a number of tiered therapies may be delivered beginning with anti-tachycardia pacing therapies and escalating to more aggressive shock therapies until the tachycardia is terminated. Termination of a tachycardia is commonly referred to as "cardioversion." Ventricular fibrillation (VF) is a serious life-threatening condition and is normally treated by immediately delivering high-energy shock therapy. Termination of VF is normally referred to as "defibrillation."

In current implantable cardioverter defibrillators, the physician programs the particular anti-arrhythmia therapies into the device ahead of time, and a menu of therapies is typically provided. For example, on initial detection of an atrial or ventricular tachycardia, an anti-tachycardia pacing therapy may be selected and delivered to the chamber in which the tachycardia is diagnosed or to both chambers. On redetection of tachycardia, a more aggressive anti-tachycardia pacing therapy may be scheduled. If repeated attempts at anti-tachycardia pacing therapies fail, a higher energy cardioversion pulse may be selected.

Reliable ICD performance depends on accurate detection of arrhythmias. A delivered therapy is generally painful to the patient and depletes the battery charge. Inappropriately delivered therapies can induce arrhythmias in some patients. It is desirable, therefore, to avoid delivering a therapy due to inappropriate arrhythmia detection. For example, it is undesirable to deliver cardioversion therapy during normal, sinus tachycardia that is a heart rate increase in response to exercise. In addition, supraventricular tachycardias, which include atrial tachycardia, atrial flutter, or atrial fibrillation, may be conducted to the ventricles and detected as ventricular tachycardia or fibrillation, resulting in the delivery of a ventricular cardioversion or defibrillation therapy when no ventricular therapy may be desired.

One approach to detecting arrhythmias is based on monitoring sensed event intervals. Monitoring of sensed intervals generally involves identifying the event intervals and event rates as they occur and applying a preset group of criteria, which must be met in order to detect a particular arrhythmia. Criteria for identifying various arrhythmias may all be monitored simultaneously. An arrhythmia detection and classification system generally disclosed, in U.S. Pat. No. 5,342,402, issued to Olson et al., incorporated herein by reference in its entirety, uses criteria for sensed events, event intervals, and event rates and is employed in the Medtronic Model 7219 devices.

Certain arrhythmias may be difficult to detect based on event intervals alone. Some patients may experience ventricular tachycardia and ventricular fibrillation having similar rates or varying rates. In other cases, a high ventricular rate may in fact be due to a supraventricular arrhythmia. Criteria for arrhythmia detection may overlap. An arrhythmia detection and classification system that employs a prioritized set of inter-related rules for arrhythmia detection is generally disclosed in U.S. Pat. No. 5,545,186, issued to Olson et al., incorporated herein by reference in its entirety. The highest priority rule that is satisfied at a given time controls the behavior of the device in regard to the delivery or withholding of therapy. This methodology includes classification of sensed events into a limited number of event patterns. Certain sequences of event patterns are strongly indicative of specific types of heart rhythms. A dual-chamber Interval-based arrhythmia detection scheme of this type has been labeled PR Logic™ and is available in all Medtronic dual chamber implantable cardioverter defibrillator devices (ICDs) since introduction of the Jewel AF® and Gem DR® brand models. This interval-based algorithm generally achieves high specificity in discriminating ventricular and supraventricular arrhythmias while maintaining high sensitivity to detecting ventricular arrhythmias overall. In order to improve the specificity of the arrhythmia classification, specific criteria have been developed for effectively identifying the likely occurrence of supraventricular tachycardias and for identifying the likelihood that events sensed in the atrium are in fact far field R-waves rather than P-waves.

However, there are some arrhythmias that are known to cause detection challenges for interval based detection algorithms, such as that used by the PR Logic™ approach. The incidence of these inappropriate detections is described in an article by Wilkoff, et al., (Circulation. 2001; 103:381–386). Certain types of supraventricular tachycardias (SVTs) producing ventricular rates in the VT/VF detection zones may potentially be detected as VT or VF. One rhythm that may be inappropriately detected as VT according to interval-based detection schemes is atrial fibrillation that is rapidly conducted to the ventricles. This SVT may be detected as a double tachycardia (simultaneous ventricular and atrial tachycardia) resulting in delivery of a VT therapy.

Another example is ventricular tachycardia with long 1:1 retrograde conduction to the atria resulting in relatively regular P-R intervals that resemble a sinus tachycardia rhythm. In this case, the ventricular tachycardia may go undetected and VT therapy may be inappropriately withheld.

In the reverse situation, sinus tachycardia or atrial tachycardia with long PR intervals may resemble ventricular tachycardia with 1:1 retrograde conduction, potentially resulting in inappropriate VT detection and unneeded delivery of VT therapy.

During AV nodal re-entrant tachycardia, nearly simultaneous P and R sensing may occur. When atrial sensed events occur sometimes before and sometimes after the ventricular sensed event, this rhythm might cause inappropriate VT detection. Simultaneous atrial fibrillation and polymorphic VT may have a P and R interval similar to rapidly conducted AF. Thus, this rhythm may be inappropriately classified as an SVT causing the polymorphic VT to go undetected.

An alternative approach to interval-based arrhythmia detection relies on the use of EGM morphology analysis alone to discriminate a normal EGM morphology from an abnormal EGM morphology. U.S. Pat. No. 6,393,316, issued to Gillberg et al, incorporated herein by reference in its entirety, generally discloses a method and apparatus that uses a wavelet transform to discriminate normal and aberrantly conducted depolarizations. Discrimination of QRS complexes during ventricular tachycardia from normal QRS complexes during supraventricular tachycardia may be achieved using an EGM morphology analysis. Wavelet transform analysis, as well as other morphology analysis methods, generally require greater processing time and power than interval-based detection methods. However, accuracy of morphology-based detection algorithms alone may be limited due to myopotential noise, low amplitude EGM signals, waveform alignment error, and rate-dependent aberrancy. Reference is made to Swerdlow C D, et al., J Cardiovasc Electrophysiol. 2002; 13(5):442–3.

It is recognized, therefore, that an improved system and methodology is desired to address challenges in arrhythmia detection. In particular, a method and apparatus is needed for improving the specificity of supraventricular tachycardia discrimination without compromising the sensitivity for detecting ventricular arrhythmias.

SUMMARY OF THE INVENTION

The present invention is directed to a method and apparatus for improving the detection of certain cardiac rhythms by combining dual chamber interval-related detection methods with electrogram morphology analysis. A prioritized set of rules are defined wherein each rule is directed at identifying a particular arrhythmia or type of arrhythmia. Each rule includes clauses that may be related to sensed event intervals and interval patterns and at least one rule includes at least one clause relating to the EGM morphology.

EGM morphology analysis is performed to discriminate normally conducted ventricular depolarizations (seen as QRS complexes on the EGM signal) from depolarizations originating in the ventricles to improve the specificity of VT discrimination from sinus tachycardia or SVT. In one embodiment, a method is provided in which dual chamber cardiac detection algorithms are combined with wavelet-based detection algorithms. In an alternative embodiment, a method is provided in which dual chamber interval-based cardiac detection algorithms are combined with QRS width discrimination of normal and abnormal QRS complexes. In one aspect of the invention there is provided a method to detect when a double tachycardia is present based on dual chamber interval patterns and morphology analysis. Another aspect of the invention includes a method of detecting when VT is present along with 1:1 retrograde conduction that cannot be discriminated from sinus tachycardia or other 1:1 supraventricular tachycardias on the basis of dual-chamber interval detection algorithms alone. Another aspect of the invention includes a method of addressing the situation when non-specific supraventricular tachycardia is discriminated from interval-detected VT based on interval and morphology-based criteria. Thus, the present invention leverages the robustness of dual-chamber interval analysis for arrhythmia classification and enhances this analysis with morphology-related information in situations where dual-chamber interval information alone is known to be equivocal in classifying an arrhythmia.

According to an embodiment of the present invention, an implantable medical device includes means for sensing cardiac events, means for applying interval only logic steps to determine cardiac rhythms in response to the sensed cardiac events, means for combining morphology based considerations of the cardiac rhythms with the interval only logic steps to achieve improved specificity in arrhythmia detection of the apparatus without loss of sensitivity, and means for delivering therapy in response to the means for combining.

According to another embodiment of the present invention, an implantable medical device includes means for sensing cardiac events, means for applying interval only logic steps to determine cardiac rhythms in response to the sensed cardiac events, means for combining interval only logic steps for determining whether the cardiac rhythms correspond to a double tachycardia and morphology of the cardiac rhythms to determine whether the cardiac rhythms correspond to a double tachycardia, and combining interval only logic steps for sinus tachycardia or other 1:1 SVT and morphology of the cardiac rhythms to determine whether VF/FVT/VT with 1:1 VA is satisfied, and determining whether the cardiac rhythms have a morphology that corresponds to sinus rhythm and whether an RR interval is greater than or equal to a PP interval, and means for delivering therapy in response to the means for combining.

DETAILED DESCRIPTION OF THE INVENTION

The present invention combines event interval and electrogram (EGM) morphology analysis in a prioritized rule-based methodology to reduce the likelihood of false positive or false negative arrhythmia detections. In particular, the present invention is directed to reducing the likelihood of false positive or false negative ventricular tachycardia or ventricular fibrillation detections in the presence of supraventricular arrhythmias. However, it is understood that the present invention may be adapted for use in a number of rule-based arrhythmia detection schemes for improving detection specificity and maintaining or improving detection sensitivity.

Dual chamber ICDs provide an opportunity for sensing both atrial and ventricular events and, through analysis of P and R patterns, allow discrimination of SVT from VT in many cases. The present invention takes advantage of this opportunity and further enhances a pattern and interval based arrhythmia detection methodology with the addition of morphology analysis to improve the discrimination of SVT from VT. The present invention is therefore preferably embodied in a dual chamber ICD, such as the ICD shown in FIG. 1.

Figure 1:
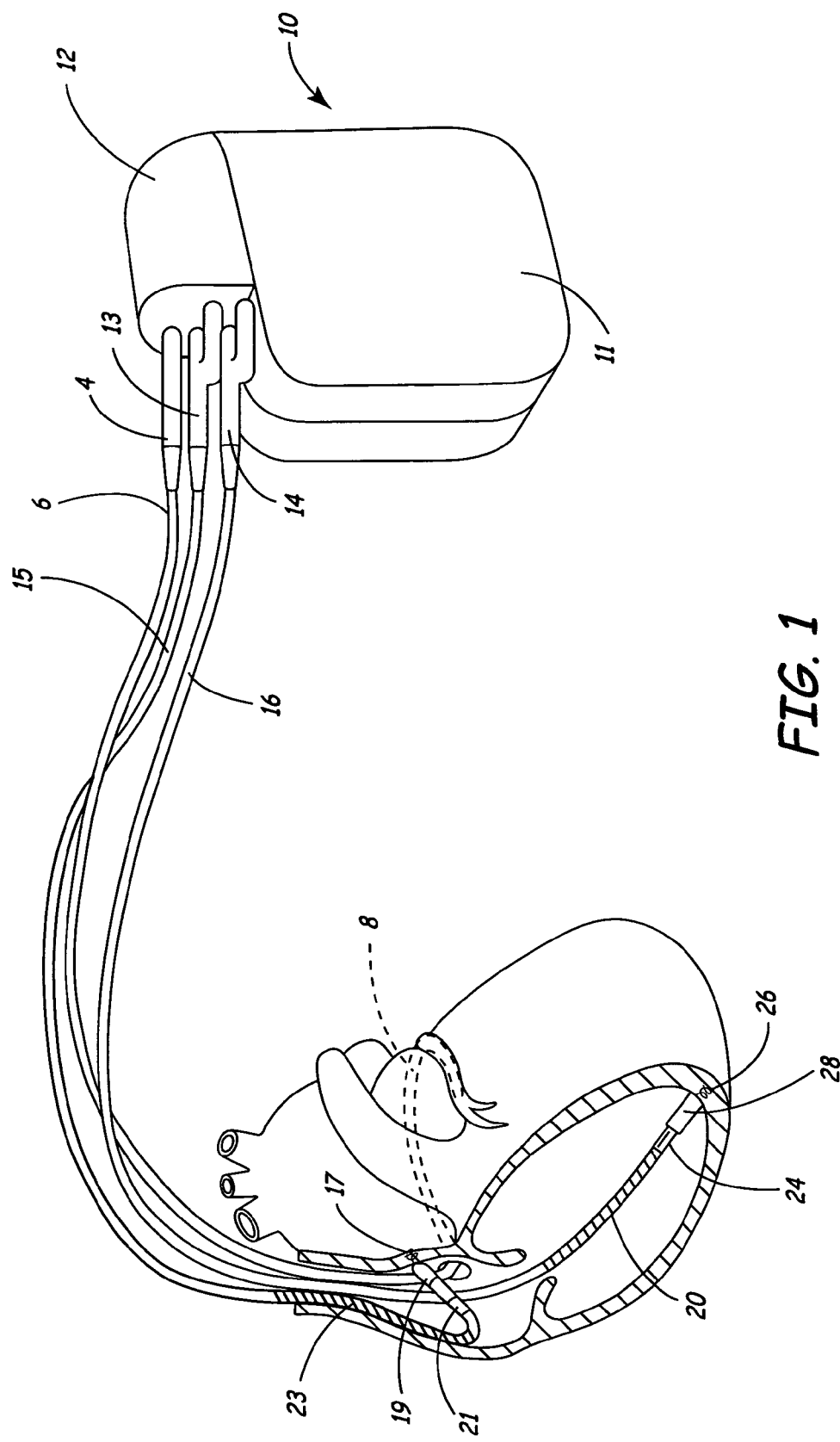
FIG. 1 is a schematic diagram of an implantable medical device for implementing the method of detecting and treating arrhythmias according to the present invention.

FIG. 1 is a schematic diagram of an implantable medical device for implementing the method of detecting and treating arrhythmias according to the present invention. As illustrated in FIG. 1, an implantable medical device, such as an implantable pacemaker cardioverter defibrillator 10, for example, is coupled to a patient's heart by way of three leads 6, 15, and 16. A connector block 12 receives the proximal end of a right ventricular lead 16, a right atrial lead 15 and a coronary sinus lead 6, used for positioning electrodes for sensing and stimulation in three or four heart chambers. In FIG. 1, the right ventricular lead 16 is positioned such that its distal end is in the right ventricle for sensing right ventricular cardiac signals and delivering pacing or shocking pulses in the right ventricle. For these purposes, right ventricular lead 16 is equipped with a ring electrode 24, an extendable helix electrode 26 mounted retractably within an electrode head 28, and a coil electrode 20, each of which are connected to an insulated conductor (not shown) contained within the body of lead 16. The proximal end of the insulated conductors are coupled to corresponding connectors carried by bifurcated connector 14 at the proximal end of lead 16 for providing electrical connection to the ICD 10.

The right atrial lead 15 is positioned such that its distal end is in the vicinity of the right atrium and the superior vena cava. Lead 15 is equipped with a ring electrode 21 and an extendable helix electrode 17, mounted retractably within electrode head 19, for sensing and pacing in the right atrium. Lead 15 is further equipped with a coil electrode 23 for delivering high-energy shock therapy. The ring electrode 21, the helix electrode 17 and the coil electrode 23 are each connected to an insulated conductor (not shown) within the body of the right atrial lead 15. Each insulated conductor is coupled at its proximal end to a connector carried by bifurcated connector 13.

The coronary sinus lead 6 is advanced within the vasculature of the left side of the heart via the coronary sinus and great cardiac vein. The coronary sinus lead 6 is shown in the embodiment of FIG. 1 as having a defibrillation coil electrode 8 that may be used in combination with either the coil electrode 20 or the coil electrode 23 for delivering electrical shocks for cardioversion and defibrillation therapies. In other embodiments, coronary sinus lead 6 may also be equipped with a distal tip electrode and ring electrode for pacing and sensing functions in the left chambers of the heart. The coil electrode 8 is coupled to an insulated conductor within the body of lead 6, which provides connection to the proximal connector 4.

The electrodes 17 and 21 or 24 and 26 may be used as bipolar pairs, commonly referred to as a "tip-to-ring" configuration, or individually in a unipolar configuration with the device housing 11 serving as the indifferent electrode, commonly referred to as the "can" or "case" electrode. The device housing 11 may also serve as a subcutaneous defibrillation electrode in combination with one or more of the defibrillation coil electrodes 8, 20 or 23 for defibrillation of the atria or ventricles. It is recognized that alternate lead systems may be substituted for the three lead system illustrated in FIG. 1. While a particular multi-chamber ICD and lead system is illustrated in FIG. 1, methodologies included in the present invention may be adapted for use with other dual chamber, or multichamber ICD systems.

Figure 2:
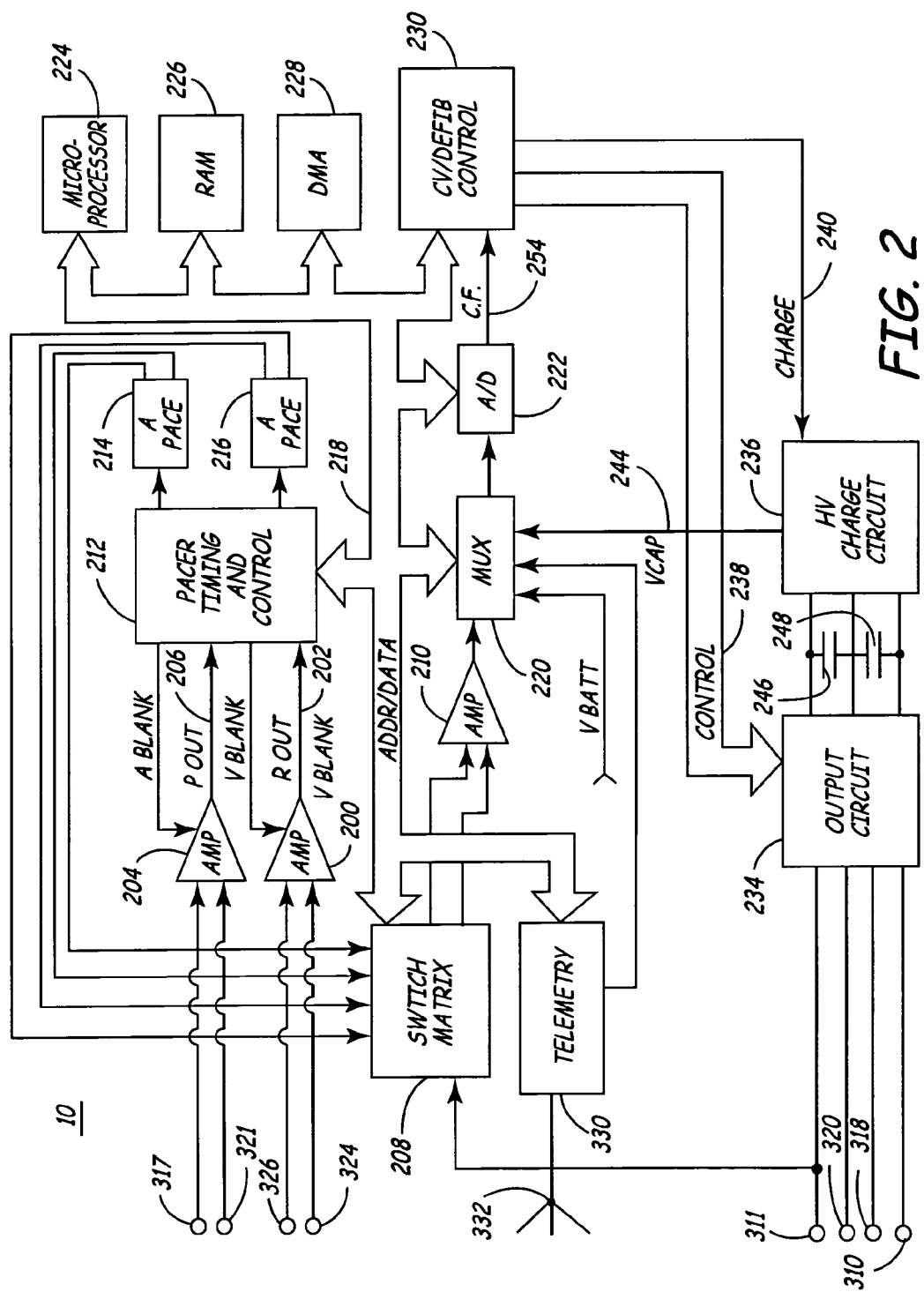
FIG. 2 is a functional block diagram of an implantable medical device in which the present invention may usefully be practiced.

FIG. 2 is a functional block diagram of an implantable cardioverter defibrillator in which the present invention may usefully be practiced. This diagram should be taken as exemplary of the type of device with which the invention may be embodied and not as limiting, as it is believed that the invention may usefully be practiced in a wide variety of device implementations, including cardioverters and defibrillators which do not provide anti-tachycardia pacing therapies or do not include bradycardia pacing, anti-tachycardia pacers which do not provide cardioversion or defibrillation, and devices which deliver different forms of anti-arrhythmia therapies such as nerve stimulation or drug administration. Methods included in the present invention may alternatively be implemented in monitoring-only devices which are capable of dual chamber sensing but do not deliver any type of therapy. The disclosed embodiment shown in FIG. 2 is a microprocessor-controlled device, but the methods of the present invention may also be practiced with devices employing dedicated digital circuitry for controlling some device functions.

With regard to the electrode system illustrated in FIG. 1, the ICD 10 is provided with a number of connection terminals for achieving electrical connection to the cardiac leads 6, 15, and 16 and their respective electrodes. The connection terminal 311 provides electrical connection to the housing 11 for use as the indifferent electrode during unipolar stimulation or sensing. The connection terminals 320, 310, and 318 provide electrical connection to coil electrodes 20, 8 and 23 respectively. Each of these connection terminals 311, 320, 310, and 318 are coupled to the high voltage output circuit 234 to facilitate the delivery of high energy shocking pulses to the heart using one or more of the coil electrodes 8, 20, and 23 and optionally the housing 11.

The connection terminals 317 and 321 provide electrical connection to the helix electrode 17 and the ring electrode 21 positioned in the right atrium. The connection terminals 317 and 321 are further coupled to an atrial sense amplifier 204 for sensing atrial signals such as P-waves. The connection terminals 326 and 324 provide electrical connection to the helix electrode 26 and the ring electrode 24 positioned in the right ventricle. The connection terminals 326 and 324 are further coupled to a ventricular sense amplifier 200 for sensing ventricular signals.

The atrial sense amplifier 204 and the ventricular sense amplifier 200 preferably take the form of automatic gain controlled amplifiers with adjustable sensing thresholds. The general operation of the ventricular sense amplifier 200 and the atrial sense amplifier 204 may correspond to that disclosed in U.S. Pat. No. 5,117,824, by Keimel, et al., incorporated herein by reference in its entirety. Whenever a signal received by atrial sense amplifier 204 exceeds an atrial sensing threshold, a signal is generated on the P-out signal line 206. Whenever a signal received by the ventricular sense amplifier 200 exceeds a ventricular sensing threshold, a signal is generated on the R-out signal line 202.

Switch matrix 208 is used to select which of the available electrodes are coupled to a wide band amplifier 210 for use in digital signal analysis. Selection of the electrodes is controlled by the microprocessor 224 via data/address bus 218. The selected electrode configuration may be varied as desired for the various sensing, pacing, cardioversion and defibrillation functions of the ICD 10. Signals from the electrodes selected for coupling to bandpass amplifier 210 are provided to multiplexer 220, and thereafter converted to multi-bit digital signals by A/D converter 222, for storage in random access memory 226 under control of direct memory access circuit 228. Microprocessor 224 employs the digitized EGM signal stored in random access memory 226 in conjunction with the morphology analysis method of the present invention. For example, the microprocessor 224 may analyze the EGM stored in an interval extending from approximately 100 milliseconds previous to the occurrence of an R-wave detect signal on R-out line 202 until approximately 100 milliseconds following the occurrence of the R-wave detect signal. The operation of the microprocessor 224 in performing the discrimination methods of the present invention is controlled by executable software stored in a computer readable medium, such as RAM 226, ROM, CD-ROMS Flash ROMS, conventional hard disks or floppy disks, for example, associated with microprocessor 224.

The telemetry circuit 330 receives downlink telemetry from and sends uplink telemetry to an external programmer, as is conventional in implantable anti-arrhythmia devices, by means of an antenna 332. Data to be uplinked to the programmer and control signals for the telemetry circuit 330 are provided by microprocessor 224 via address/data bus 218. Received telemetry is provided to microprocessor 224 via multiplexer 220. Numerous types of telemetry systems known for use in implantable devices may be used.

The remainder of circuitry illustrated in FIG. 2 is dedicated to the provision of cardiac pacing, cardioversion and defibrillation therapies and, for the purposes of the present invention, may correspond to circuitry known in the prior art. In the exemplary embodiment shown in FIG. 2, the pacer timing and control circuitry 212 includes programmable digital counters which control the basic time intervals associated with various single, dual or multi-chamber pacing modes or anti-tachycardia pacing therapies delivered in the atria or ventricles. Pacer circuitry 212 also determines the amplitude of the cardiac pacing pulses under the control of microprocessor 224.

During pacing, escape interval counters within pacer timing and control circuitry 212 are reset upon sensing of R-waves or P-waves as indicated by signals on lines 202 and 206, respectively. In accordance with the selected mode of pacing, pacing pulses are generated by atrial pacer output circuit 214 and ventricular pacer output circuit 216. The pacer output circuits 214 and 216 are coupled to the desired electrodes for pacing via switch matrix 208. The escape interval counters are reset upon generation of pacing pulses, and thereby control the basic timing of cardiac pacing functions, including anti-tachycardia pacing.

The durations of the escape intervals are determined by microprocessor 224 via data/address bus 218. The value of the count present in the escape interval counters when reset by sensed R-waves or P-waves can be used to measure R-R intervals, P-P intervals, P-R intervals, and R-P intervals, which measures are stored in memory 226 and used in conjunction with the present invention to diagnose the occurrence of a variety of arrhythmias, as discussed in detail below.

Microprocessor 224 operates as an interrupt driven device, and is responsive to interrupts from pacer timing and control circuitry 212 corresponding to the occurrences of sensed P-waves and R-waves and corresponding to the generation of cardiac pacing pulses. These interrupts are provided via data address bus 218. Any necessary mathematical calculation or logic operations to be performed by microprocessor 224, including those to be described in greater detail below, and any updating of values or intervals controlled by pacer timing and control circuitry 212 take place following such interrupts. These operations are performed under the control of software stored in ROM associated with microprocessor 224. A portion of the random access memory 226 may be configured as a number of recirculating buffers capable of holding a series of measured intervals, which may be analyzed in response to a pace or sense interrupt by microprocessor 224 for diagnosing an arrhythmia as will be further described below. The arrhythmia detection method of the present invention may include prior art arrhythmia detection algorithms. As described below, arrhythmia detection methodology presently available in Medtronic dual chamber pacemaker cardioverter defibrillators is employed as part of the arrhythmia detection and classification method according to the disclosed preferred embodiment of the invention. However, any of the various arrhythmia detection methodologies known to the art might also be usefully employed in alternative embodiments of the invention.

In response to the detection of atrial or ventricular tachycardia, an anti-tachycardia pacing therapy may be delivered if desired by loading a regimen from microcontroller 224 into the pacer timing and control circuitry 212 according to the type of tachycardia detected. Alternatively, circuitry for controlling the timing and generation of anti-tachycardia pacing pulses as generally described in U.S. Pat. No. 4,577,633 issued to Berkovits et al., U.S. Pat. No. 4,880,005 issued to Pless et al., U.S. Pat. No. 4,726,380 issued to Vollmann et al., and U.S. Pat. No. 4,587,970 issued to Holley et al, all of which patents are incorporated herein by reference in their entireties, may be used.

In the event that higher voltage cardioversion or defibrillation pulses are required, microprocessor 224 activates the cardioversion and defibrillation control circuitry 230 to initiate charging of the high voltage capacitors 246 and 248 via charging circuit 236 under the control of high voltage charging control line 240. The voltage on the high voltage capacitors 246 and 248 is monitored via a voltage capacitor (VCAP) line 244, which is passed through the multiplexer 220. When the voltage reaches a predetermined value set by microprocessor 224, a logic signal is generated on the capacitor full (CF) line 254, terminating charging. The defibrillation or cardioversion pulse is delivered to the heart by high voltage output circuit 234 under the control of the pacer timing and control circuitry 212 via a control bus 238. The output circuit 234 determines the electrodes used for delivering the cardioversion or defibrillation pulse and the pulse wave shape. Examples of high-voltage cardioversion or defibrillation output circuitry are generally disclosed in U.S. Pat. No. 4,727,877 issued to Kallok, and U.S. Pat No. 5,163,427 issued to Keimel, both incorporated herein by reference in their entirety.

One embodiment of an appropriate system for delivery and synchronization of ventricular cardioversion and defibrillation pulses and for controlling the timing function related to them is generally disclosed in commonly assigned U.S. Pat. No. 5,188,105 to Keimel, incorporated herein by reference in its entirety. If atrial defibrillation capabilities are included in the device, appropriate systems for delivery and synchronization of atrial cardioversion and defibrillation pulses and for controlling the timing function related to them may be found in PCT Patent No. WO92/18198 to Adams, et al., and U.S. Pat. No. 4,316,472 issued to Mirowski et al., both incorporated herein by reference in their entireties.

However, any known cardioversion or defibrillation pulse control circuitry is believed usable in conjunction with the present invention. For example, circuitry controlling the timing and generation of cardioversion and defibrillation pulses as disclosed in U.S. Pat. No. 4,384,585, issued to Zipes, U.S. Pat. No. 4,949,719, issued to Pless et al., and in U.S. Pat. No. 4,375,817, issued to Engle et al., all incorporated herein by reference in their entireties may also be employed.

In modern implantable cardioverter defibrillators, the particular therapies are programmed into the device ahead of time by the physician, and a menu of therapies is typically provided. For example, on initial detection of tachycardia, an anti-tachycardia pacing therapy may be selected. On redetection of tachycardia, a more aggressive anti-tachycardia pacing therapy may be scheduled. If repeated attempts at anti-tachycardia pacing therapies fail, a higher-level cardioversion pulse therapy may be selected thereafter. Prior art patents illustrating such pre-set therapy menus of anti-tachycardia therapies include the above-cited U.S. Pat. No. 4,726,380 issued to Vollmann et al., above cited U.S. Pat. No. 4,587,970 issued to Holley et al., and U.S. Pat. No. 4,830,006 issued to Haluska, incorporated herein by reference in their entirety.

Figure 3:
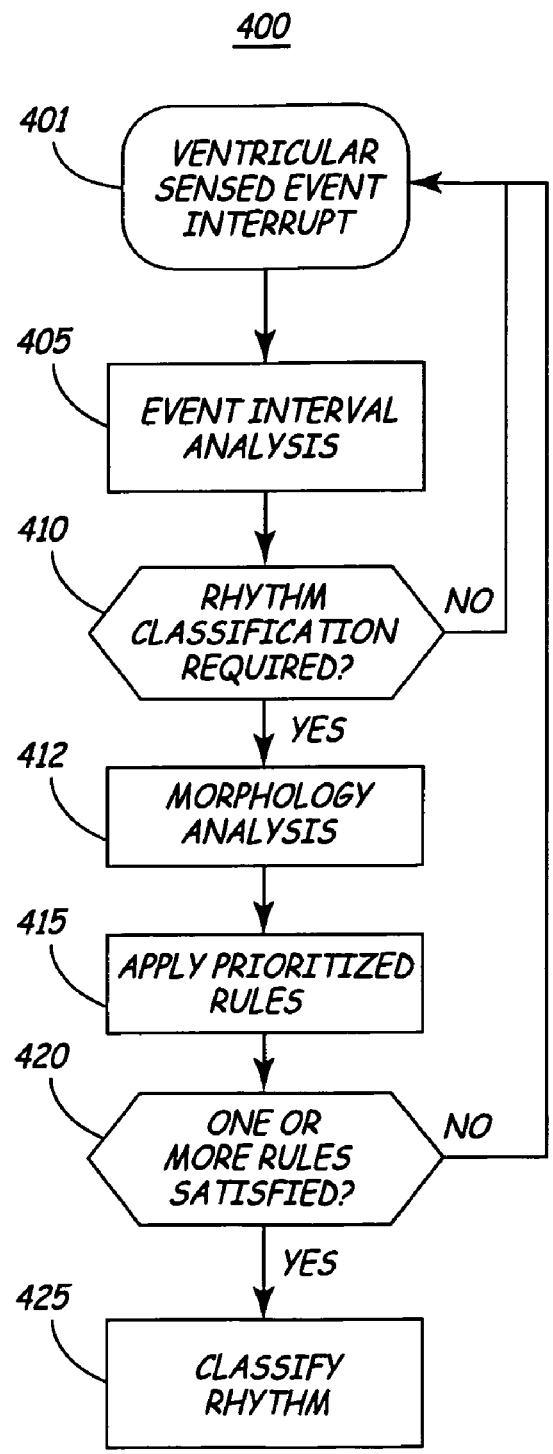
FIG. 3 is a flow chart of an arrhythmia detection method according to the present invention.

FIG. 3 is a flow chart of an arrhythmia detection method according to the present invention. According to a preferred embodiment of the present invention, both a prioritized, rule-based algorithm including heart rhythm classification criteria related to dual chamber event interval analysis and EGM morphology analysis are utilized to discriminate between arrhythmias. This combined approach is taken to address problematic arrhythmias involved in discriminating between arrhythmias using interval-based or morphology-based methodologies alone. For example, the present invention combines the use of morphology analysis and the prioritized rule-based algorithm for classifying the heart rhythm as generally disclosed in the above-cited U.S. Pat. No. 5,545,186 issued to Olson et al., and incorporated herein by reference in its entirety.

As noted above, an interrupt signal sent to microprocessor 224 with the occurrence of each sensed ventricular event, indicated at step 401 of FIG. 3, will cause an analysis of event intervals at step 405. As will be described in greater detail below, a number of counts and interval-related values are updated at step 405. These interval-related values and the outputs of various counters, which may include continuous recognition machines, will be available to the microprocessor in applying dual-chamber, interval-related criteria used for classifying a heart rhythm.

At step 410, criteria may optionally be applied for determining when the prioritized, rule-based classification system, including dual chamber event interval and EGM morphology analysis, should be activated. Such activating criteria may be applied in order to avoid microprocessor intensive functions for evaluating EGM morphology when those function are not needed for discriminating heart rhythms. In one embodiment, detection of a fast rate may be required before performing an EGM analysis and applying the prioritized rules. In another embodiment, the absence of any of a set of benign rhythms may trigger an EGM analysis and application of prioritized rules. Reference is made to commonly assigned U.S. patent application Ser. No. 10/023, 234 to Stadler et al, filed Dec. 18, 2001.

If the rule based classification system is activated, an EGM morphology analysis is performed, step 412. In a preferred embodiment, the morphology analysis is performed when a fast ventricular rate is detected to determine whether the currently sensed ventricular event possesses morphological characteristics substantially equal to a normal QRS complex associated with sinus rhythm. If the sensed ventricular event has morphological characteristics determined to be substantially different than a normal QRS complex, the ventricular event is classified as "abnormal" and is likely to be associated with ventricular tachycardia or fibrillation. After determining whether the sensed ventricular event is substantially equal to a sinus QRS complex, morphology counters are updated which track the number of "normal" and "abnormal" ventricular sensed events. The values of these morphology counters will be available to the microprocessor in applying morphology-related criteria used for classifying a heart rhythm.

In addition to the morphology analysis, a number of prioritized rules are applied, step 415, which include criteria relating to the event interval analysis performed at step 405 and the EGM morphology analysis performed at step 410. As noted above, application of the rules at step 415 may be triggered by a detection of a fast rate or other pre-screening criteria utilized at decision step 410. In a preferred embodiment, the prioritized rule-based algorithm for classifying the heart rhythm includes dual-chamber interval pattern criteria as generally disclosed in the above-cited U.S. Pat. No. 5,545,186 issued to Olson et al., and as currently implemented in commercially available Medtronic dual chamber implantable cardioverter defibrillators as PR Logic™. The prioritized rules applied at step 415 further include, in accordance with the present invention, EGM morphology criteria. In the context of the specific embodiment disclosed herein, several possible rhythm classifications are provided by a rule set with each rule including a number of criteria, or "clauses" that must be met in order for the rule to be satisfied. Application of multiple rules following a ventricular sensed event allows for the possibility of more than one rule to be satisfied at a given time. The rule set is therefore assigned a prioritized order such that the highest priority rule that is satisfied at a given time is used to classify the heart rhythm, thus determining the device response to the identified rhythm.

If no rules are satisfied, as determined at step 420, microprocessor 224 returns to step 401 to await the next ventricular sensed event interrupt and continue with the collection of interval and morphology data. If one or more rules are satisfied at step 420, then the highest priority rule having all clauses satisfied, which may relate to both dual-chamber event intervals and morphology, is used to classify the heart rhythm at step 425. Programmed therapies, which may include anti-tachycardia pacing, or cardioversion or defibrillation shocks, are then delivered or withheld according to the detected rhythm.

Figure 4:
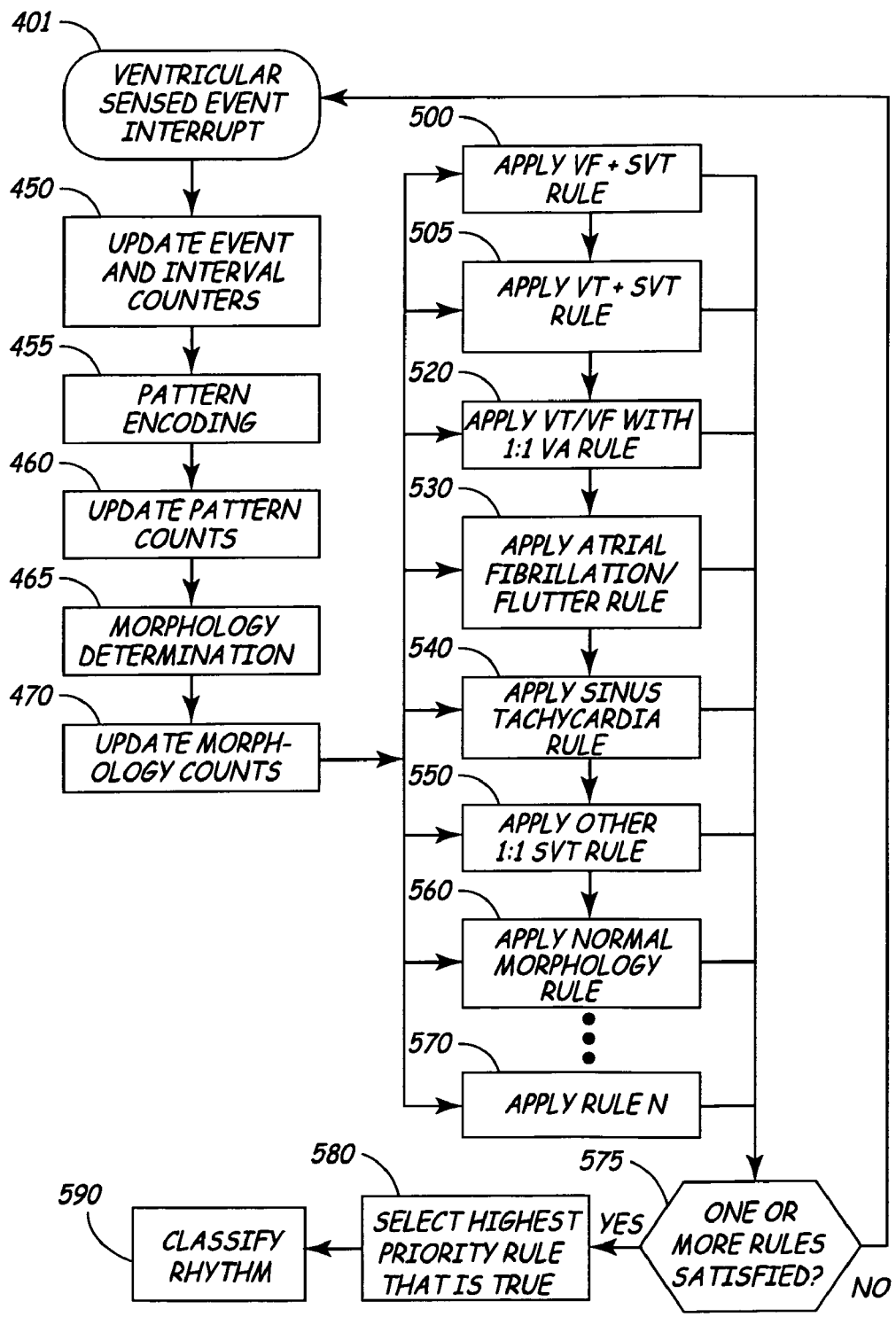
FIG. 4 is a flow chart illustrating in greater detail steps included in the method of FIG. 3, which combines event interval and morphology-related clauses in a prioritized rule-based scheme for detecting and classifying arrhythmias.

FIG. 4 is a flow diagram illustrating in greater detail steps included in the arrhythmia detection method of FIG. 3, which combines dual chamber event interval and morphology-related clauses in a prioritized rule-based scheme for detecting and classifying arrhythmias. After detecting a ventricular sensed event at step 401, event counters, interval counters, determination of median intervals, such as a median R-R interval, median P-P interval, and other values that will be used in applying rate and interval-related criteria contained in the prioritized rule set are updated at step 450.

At step 455, the timing of atrial and ventricular events occurring during the preceding two R-R intervals is analyzed to develop a "pattern code." R-R intervals are divided into time zones such that P-R intervals may be classified according to the time zone in which the P-wave occurs, relative to the R-wave. In an exemplary embodiment, each of two R-R intervals is divided into four zones. Zone 1 encompasses the first 50 milliseconds following the ventricular event initiating the R-R interval. Zone 2 extends from the end of zone 1 until halfway through the R-R interval. Zone 3 extends from halfway through the R-R interval to 80 milliseconds prior to the sensed ventricular event ending the R-R interval and zone 4 includes the last 80 milliseconds of the R-R interval.

In order to determine the pattern codes, each individual R-R interval is assigned a "beat code" based on the number of occurrences of atrial events during the R-R interval and their location relative to the R-waves. The number of atrial events occurring in the R-R interval, referred to as the P-count, the duration of the R-P interval and the duration of the P-R interval for each atrial event associated with the R-R interval are evaluated in order to assign each R-R interval a beat code.

Two R-R intervals are evaluated to determine the corresponding beat codes, and the resulting beat code pairs are assigned a pattern code. Details regarding pattern codes are described in the above-cited U.S. Pat. No. 5,454,186 and will therefore not be fully described herein. In summary, each beat code pair defines a pattern code and a sequence of pattern codes, referred to as a "grammar" is indicative of the heart rhythm present. The presence of a particular arrhythmia can be evidenced by a particular grammar.

At step 450, continuous recognition machines output a count indicative of the degree of correspondence of the sensed rhythm to the defined grammars for each arrhythmia to be detected. Rules for identifying the various arrhythmias include clauses setting forth criteria against which the output counts of the continuous recognition machine are compared. Look-up tables are employed in conjunction with the continuous recognition machine for recognizing pattern code sequences corresponding to, for example, normal sinus rhythm, sinus tachycardia, atrial fibrillation or flutter, atrial-venticular nodal tachycardia, and simultaneous ventricular and supraventricular tachycardia. In alternative embodiments, other counters may be implemented in addition to or in place of continuous recognition machines for tracking interval patterns indicative of a particular arrhythmia. For example, an AF counter may be substituted for a continuous recognition machine for counting up when there is evidence of atrial fibrillation during an R-R interval (such as a P-count of 2), counting down when there is contrary evidence (such as a P-count of 0), and remaining unchanged when the situation is ambiguous (such as a P-count of 2 but evidence of far-field R-waves). Reference is made to U.S. Pat. No. 6,259,947 issued to Olson et al., incorporated herein by reference in its entirety.

At step 465, the EGM morphology is analyzed to allow morphology counts of normal and abnormal morphology to be updated at step 470. EGM morphology analysis may be performed only when rhythm classification is required based on activation criteria as described above. In one embodiment, the morphology determination performed at step 465 includes performing a wavelet transform of the sensed signal as generally disclosed in the above-cited U.S. Pat. No. 6,393,316 to Gillberg et al., incorporated herein by reference in its entirety. Reference is also made to Koyrakh L., et al., "Wavelet transform based algorithms for EGM morphology discrimination of implantable ICDs," Computers in Cardiology. 2000;26:343–346. Alternative methods for comparing waveforms include using an area of distance or a correlation waveform analysis metric, as also described in the above-cited Gillberg patent.

The wavelet transform method is fundamentally based on "template matching", a mathematical comparison of a known template EGM signal to the EGM signal from an unknown rhythm. In accordance with the present invention, this comparison forms the basis for certain clauses contained in the rule set for discriminating VT from SVT or sinus tachycardia. A wavelet transform is a mechanism for describing the evolution over time of signal frequency content unlike the commonly known Fourier transform that assumes frequency content to be time-invariant.

This wavelet transform embodiment includes creating a template of a "normal" EGM signal during sinus rhythm. Wavelet transform coefficients are computed from the "normal" EGM, and the wavelet coefficients that describe the salient features of the waveform are extracted to create a "normal" template that is stored in the memory of the implanted device. During a fast rhythm, an "unknown" EGM waveform is processed by performing a wavelet transform to determine if wavelet transform coefficients of the unknown EGM match coefficients of the normal template. If a match occurs, the waveform will be classified as a normal, sinus waveform. If the unknown EGM does not match the template, the waveform will be classified as "abnormal," indicating a tachyarrhythmia is likely to be present. Details regarding the methods for acquiring a normal template and performing comparisons of a wavelet transform from an unknown waveform to the template are described in the above-cited patent issued to Gillberg.

Embodiments described herein employ a normal waveform as the basis for a waveform template such that determination of waveforms that show sufficient similarity to the template may result in classification of the heart rhythm as a sinus tachycardia or SVT and a withholding of VT or VF therapy. In alternative embodiments, a defined aberrant waveform might be used as the basis for a template, e.g. a ventricular tachycardia waveform. Comparisons of unknown waveforms to such templates may form the basis of specific clauses contained in rules defined for classifying the particular type of aberrant waveform. In such embodiments, determination of waveforms that show sufficient similarity to the template might result in a VT detection and subsequent delivery of therapy. In addition, while the embodiments disclosed herein employ a single template, alternative embodiments of the present invention may employ multiple templates, each indicative of an identified heart rhythm, and form the basis of a clause contained in a rule defined for classifying the identified heart rhythm.

Template acquisition may be performed either automatically or with user supervision. Templates are preferably acquired on a patient-by-patient basis because of variability in EGM waveforms due to inter-individual variability and differences in the type and location of EGM sensing electrodes. Templates may be acquired during normal sinus rhythm or obtained from stored episode data from spontaneous SVTs or other identified heart rhythms as desired. An EGM waveform is preferably limited to the ventricular depolarization. A portion of EGM data associated with the ventricular depolarization may be taken by centering a morphology window at each ventricular sensed event as generally described in the Gillberg patent. In this embodiment, the wavelet transform is performed on the EGM data segment at step 465 to categorize the ventricular sensed event as "abnormal" or "normal", and a corresponding counter is updated at step 470.

In another embodiment of the present invention, the morphological analysis includes determination of the QRS width during an unidentified rhythm and comparing the QRS width to a normal or expected QRS width associated with normal sinus rhythm. The QRS width may then be used to classify the beat as a "normal" or "abnormal" beat. In such embodiments, one or more clauses contained in one or more rules relating to the discrimination of SVTs, VT, and sinus tachycardia may be based on the determination of normal or abnormal QRS width.

A preferred method for determining EGM width employed by the present invention is generally disclosed in U.S. Pat. No. 5,312,441 issued to Mader, et al., incorporated herein by reference in its entirety. Identification of the beginning and end points of an R-wave is accomplished by the occurrence of a series of sequential digitized signals which differ from preceding signals by more than or less than a predetermined amount. The width of the R-wave is defined as the interval between the identified beginning and end points. A width threshold may be predefined which when crossed discriminates between normally propagated R-waves which are relatively narrow and abnormally propagated R-waves which are relatively wide. In this embodiment, the QRS width for the currently sensed ventricular event would be determined at step 465 and compared to the width threshold. If the R-wave is determined as "narrow", a "normal" morphology counter is increased at step 470. If the R-wave is determined as "wide," an "abnormal" morphology counter is increased at step 470.

In alternative embodiments, other methods known in the art, or methods to be developed in the future, for performing a morphological or other analysis of EGM features that reliably distinguishes a normally conducted QRS complex from a QRS complex of ventricular origin may be successfully used in the present invention.

Having updated interval-related values, pattern-related counts, and morphology-related counts, the arrhythmia detection algorithm of FIG. 4 is ready to apply a number of prioritized rules according to the present invention represented by steps 500 through 570. In one embodiment, a set of rules included in steps 500 through 570, given in order of priority, may include:

VF+SVT rule
VT+SVT rule
VT/VF with 1:1 VA (retrograde conduction) rule
AF/A Flutter rule
Sinus Tachycardia rule
Other 1:1 SVT rule
Normal morphology rule
VF rule—7219
FVT rule—7219
VT rule—7219

In addition to adherence to defined grammars, rules applied for classifying a rhythm also employ various rate and interval based recognition criteria employed in the Medtronic Model 7219 implantable pacemaker cardioverter defibrillator. These criteria are discussed in detail in the above-cited U.S. Pat. No. 5,342,402, issued to Olson and incorporated herein by reference in its entirety. Programmable fibrillation detection interval (FDI) ranges and tachycardia detection interval (TDI) ranges designate the range of sensed event intervals indicative of fibrillation or tachycardia. Sensed event intervals falling into these ranges are counted to provide a count of tachycardia intervals and fibrillation intervals. A programmable number of intervals to detect (NID) defines the number of tachycardia intervals occurring out of a given number of preceding event intervals required to detect tachycardia. A separately programmed NID defines the number of consecutive fibrillation intervals required to detect fibrillation. In addition to the tachycardia and fibrillation interval detection criteria, rapid onset criterion and rate stability criterion may also be defined and must be satisfied before detecting tachycardia. Furthermore, a combined count of tachycardia and fibrillation intervals may be compared to a combined count threshold and, according to predefined criteria, used in detecting fibrillation or tachycardia.

Fast ventricular tachycardia may be distinguished from slow ventricular tachycardia and ventricular fibrillation. Following a provisional diagnosis of ventricular fibrillation or ventricular tachycardia, immediately preceding intervals may be examined to determine whether the provisional detection should be confirmed or amended to indicate detection of fast ventricular tachycardia.

The entire arrhythmia detection methodology of the Model 7219 is retained in the disclosed embodiment of the present invention. The criteria for detection of ventricular fibrillation, fast ventricular tachycardia, and ventricular tachycardia according to this methodology are designated as the lowest priority rules employed for arrhythmia detection and classification (see rules 8, 9 and 10 above).

The arrhythmia detection and classification scheme of the present invention also employs a measurement of R-R interval variability, as disclosed in U.S. Pat. No. 5,330,508, issued to Gunderson and incorporated herein by reference in its entirety.

According to the present invention, in conjunction with the operation of rules intended to identify the likely occurrence of ventricular and supraventricular tachycardia, microprocessor 224 keeps track of the number of R-R intervals which likely contain sensed atrial events caused by far-field R-waves, out of a preceding series of R-R intervals. In response to the occurrence of an R-R interval having a P-count equal to 2, the R-P and P-R intervals for the R-R interval are examined for evidence of far-field R-wave sensing. Details regarding a process for determining that far-field R-wave sensing is likely to be present are described in the above-cited U.S. Pat. No. 5,545,186 issued to Olson. Microprocessor 224 keeps track of the number of R-R intervals out of a preceding series of intervals that likely contain a far-field R-wave. This number is compared to a threshold value to determine whether it is likely that a heart rhythm that appears to have a high atrial rate is in fact the result of far-field R-wave sensing.

In addition, rules intended to identify the occurrence of atrial fibrillation or flutter and sinus tachycardia may include a clause relating to the degree of co-variance of measured R-P and R-R intervals as disclosed in the cited '186 patent issued to Olson. See also U.S. Pat. No. 5,991,656 issued to Olson, et al., and U.S. Pat. No. 5,755,736 issued to Gillberg et al., both patents incorporated herein by reference in their entirety.

Figure 5:
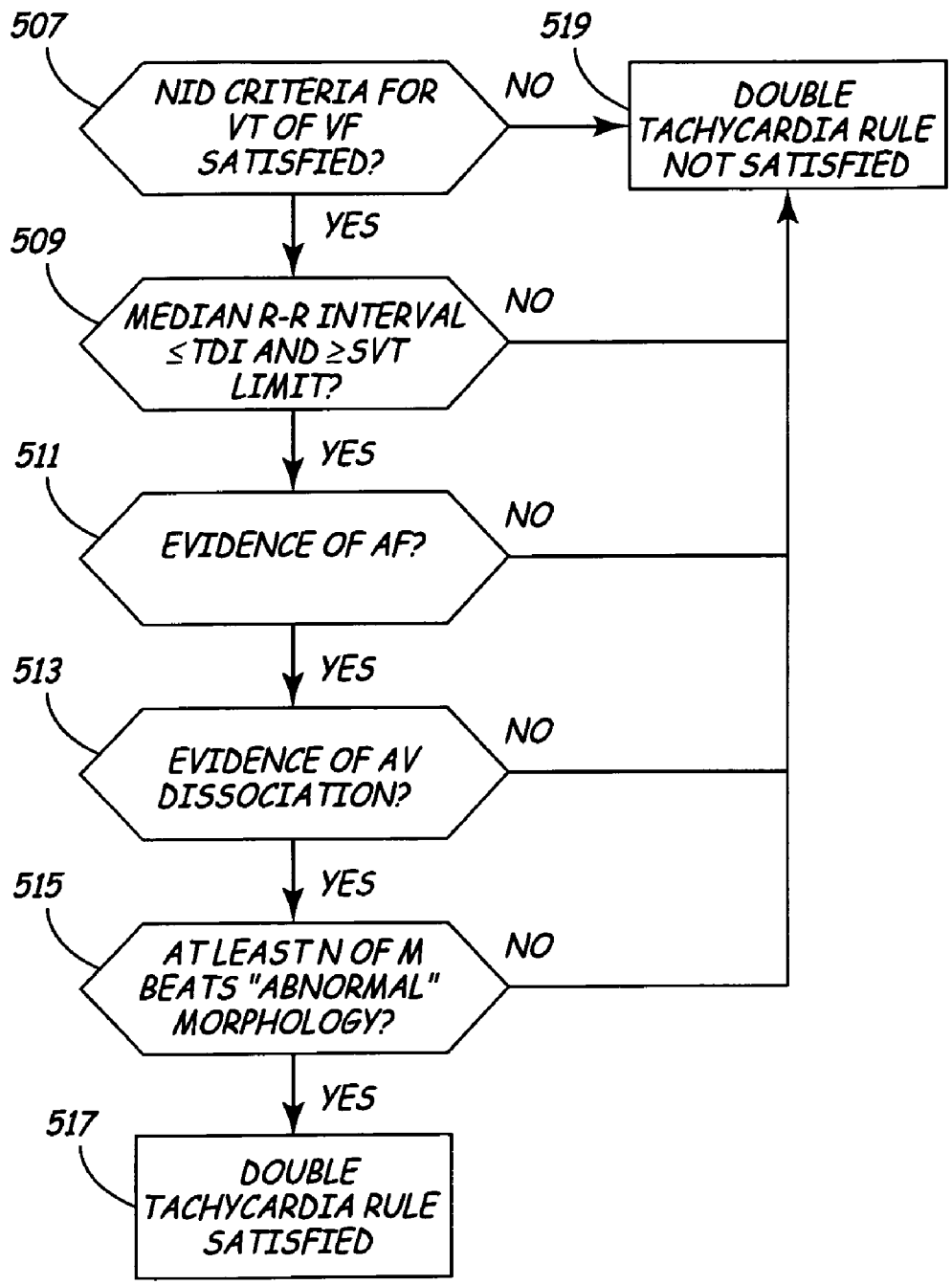
FIG. 5 is a flow chart of a double tachycardia rule according to an embodiment of the present invention.

The VF+SVT rule, listed as the highest priority rule above is applied at step 500 of FIG. 4 to detect simultaneous VF and SVT. The second priority VT+SVT rule listed above, is applied at step 505 for the detection of simultaneous VT and SVT. These rules are both related to the detection of double tachycardia and preferably include clauses relating to dual chamber intervals and EGM morphology, in accordance with the present invention. FIG. 5 summarizes clauses included in these double tachycardia rules in a preferred embodiment of the present invention.

As illustrated in FIG. 5, a first clause, at decision step 507, requires the NID criterion for detecting VT or VF to be satisfied. A second clause, at decision step 509, requires that the median R-R interval is less than the TDI and greater than an SVT limit. A median R-R interval less than the SVT limit precludes SVT detection preventing the double tachycardia rules from being satisfied. A third clause, at decision step 511, requires pattern grammar evidencing AF. A fourth clause at decision step 513 requires evidence of AV dissociation. In an exemplary embodiment for determining if AV dissociation is likely to be present, the mean of the most recent 8 P-R intervals is computed. An individual ventricular event is judged dissociated from the previous atrial event if the absolute difference between the current P-R interval and the mean P-R interval is greater than a predetermined amount, for example 40 ms, or if there are no P events in the current R-R interval. If this criterion is met for at least 4 of the last 8 ventricular events, the clause regarding evidence of AV dissociation at step 513 is satisfied. Reference is made to the above-cited U.S. Pat. No. 6,259,947 and to U.S. Pat. No. 6,141,581 issued to Olson et al., incorporated herein by reference in its entirety.

A fifth clause, at decision step 515, requires that at least a predetermined number (N) of ventricular events out of a given number (M) be determined as having "abnormal morphology." The numbers N and M may be programmable and are preferably on the order of 6 to 8 abnormal beats out of 8. Abnormal morphology may be determined according to the methods described above corresponding to either a wavelet transform method or QRS width method or other appropriate morphology analysis method. If the criteria at steps 507 through 515 are met, one of the double tachycardia rules (VF+SVT or VT+SVT) is satisfied as indicated at step 517, depending on which of the NID criterion, either for VT or VF, was satisfied at step 507. Because the double tachycardia rules are the highest priority rules, a ventricular therapy will be delivered. If any one of these clauses (steps 507 through 515) are not met, the double tachycardia rules are not satisfied, as indicated at step 519.

Figure 6:
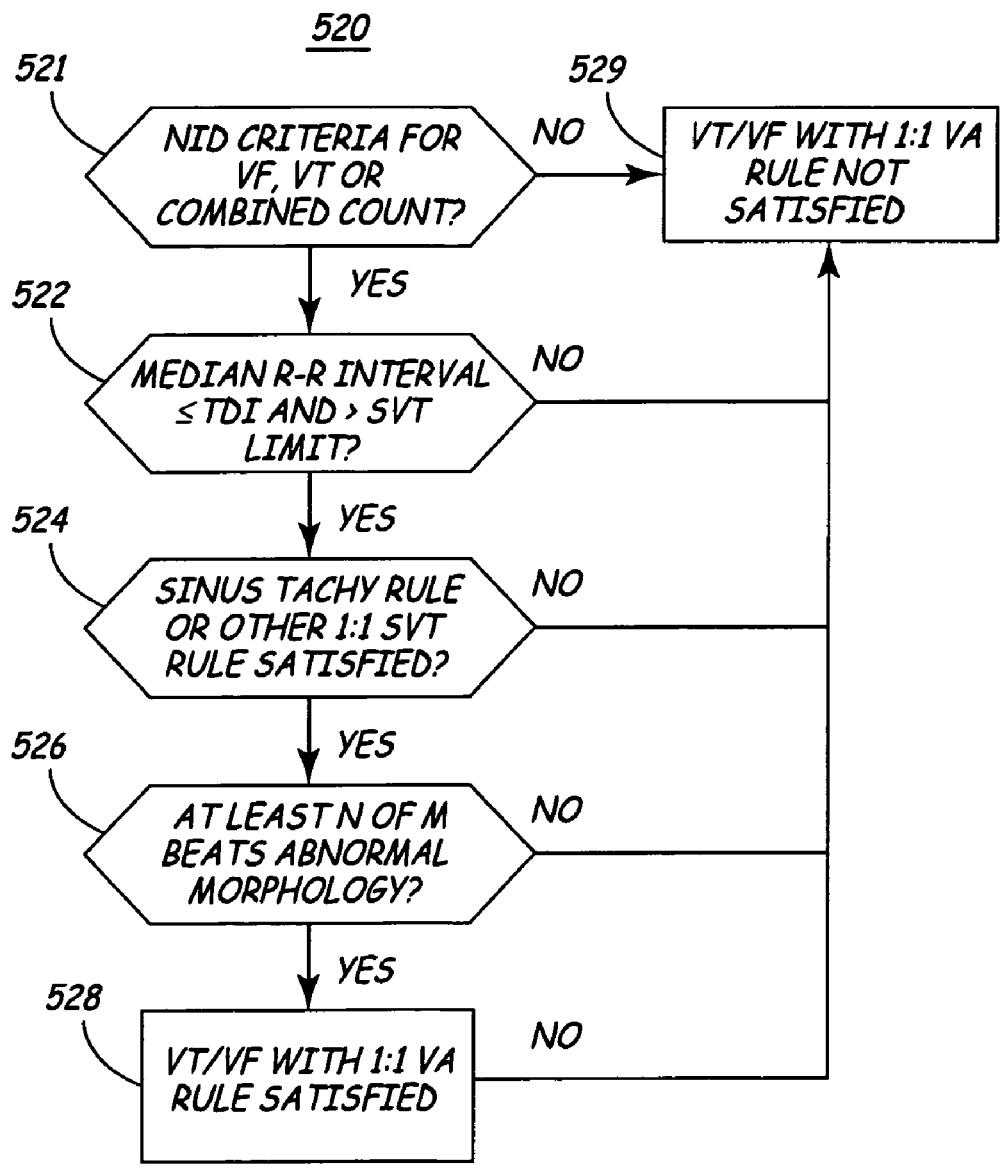
FIG. 6 is a flow chart of a VT/VF with 1:1 VA rule according to an embodiment of the present invention.

At step 520 in FIG. 4, a new rule provided by the present invention is applied to discriminate VT or VF with 1:1 retrograde (ventricular to atrial) conduction from supraventricular tachycardia or sinus tachycardia. Clauses included in the VT/VF with 1:1 VA rule are summarized in FIG. 6. As illustrated in FIG. 6, a first clause, at decision step 521, requires that the number of intervals to detect (NID) criteria is met for VF, VT or the combined interval count of VF and VT. At decision step 522, a second clause requires the median R-R interval to be less than the TDI and greater than an SVT limit. A third clause at step 524 requires that a sinus tachycardia rule or "other 1:1 SVT" rule be satisfied. These rules include rate and pattern grammar-related clauses directed at identifying sinus tachycardia or AV nodal re-entrant tachycardia. If one of these rules is satisfied, a 1:1 rate is known to be present and either of these rules would withhold therapy if no higher priority rule is satisfied. However, if a VT or VF with 1:1 retrograde conduction is present, ventricular therapy should be delivered. This rhythm, which may be difficult to discriminate from sinus tachycardia or a 1:1 SVT by interval analysis alone, may be discriminated by morphology analysis.

Thus, a fourth clause, at step 526, requires that a predetermined minimum number (N) of ventricular sensed events out of a given number (M) be determined as having abnormal morphology. The numbers N and M are preferably programmable and on the order of 6, 7 or 8 beats out of 8. The values for N and M used in this clause of the VT/VF with 1:1 VA rule may be the same or different than the values used in morphology-related clauses of other rules.

If each of these clauses (steps 521–526) are met, then the VT/VF with 1:1 VA rule is satisfied, as indicated at step 528, overruling the lower priority sinus tachycardia or other 1:1 SVT rule that has been met, and VT therapy will be delivered. If any one of these clauses (steps 521 through 526) is not met, the VT/VF with 1:1 VA rule is not satisfied as indicated at step 529.

At step 530 of FIG. 4, the AF/A flutter rule is applied. This rule, and the sinus tachycardia rule at step 540 and the "other" 1:1 SVT rule at step 550 may be implemented as provided by existing PR Logic™ algorithms. The AF/A flutter rule may include clauses requiring: a greater than 1:1 rhythm or regular 2:1 rhythm (i.e., the P count is greater than one for at least some R-R intervals or consistently 2 for all R-R intervals); R-R intervals that are irregular or, regular R-R intervals with evidence of AV association; and a lack of evidence of far-field R-wave sensing. The sinus tachycardia rule may include clauses requiring that pattern grammar indicating antegrade (atrial to ventricular) conduction is present and that consistent far field R-wave sensing is likely to be present. The "other" 1:1 SVT rule includes a clause relating to pattern grammar evidencing a junctional P-R pattern and is directed at discriminating AV nodal re-entrant tachycardias or other SVTs occurring with a 1:1 rhythm.

At step 560, a new rule provided by the present invention, referred to as the "normal morphology" rule, is applied. This rule is directed at discriminating other supraventricular tachycardias that are problematic when using an interval-based algorithm alone for detecting arrhythmias, such as atrial tachycardias with sudden heart rate onset or AV nodal re-entrant tachycardia with alternating P-R patterns. Clauses included in this rule are summarized in FIG. 7.

Figure 7:
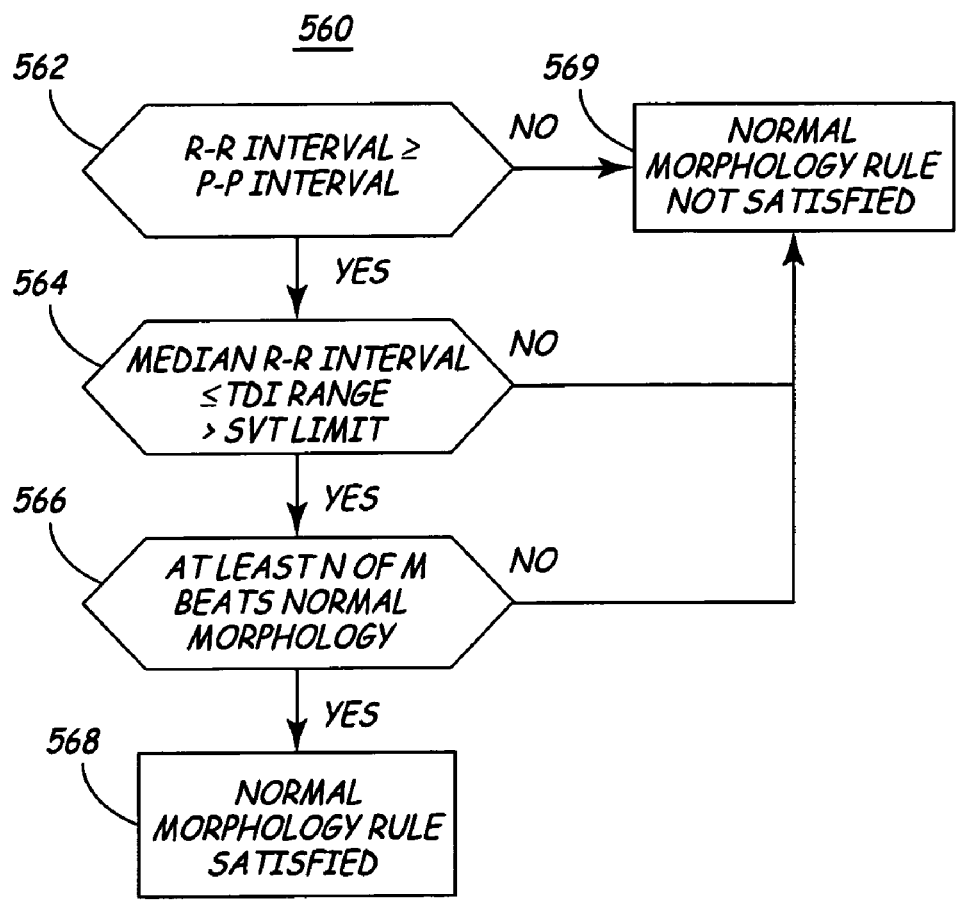
FIG. 7 is a flow chart of a normal morphology rule according to an embodiment of the present invention.

As illustrated in FIG. 7, a first clause requires that the median R-R interval be greater than or equal to the median P-P interval, step 562. At decision step 564, a second clause requires that the median R-R interval be less than the TDI and greater than the SVT limit. At step 566, a third clause requires that at least a predetermined number (N) of ventricular sensed events out of a given number (M) have a normal morphology. The numbers N and M are preferably programmable and on the order of 6, 7 or 8 beats out of 8. The values for N and M used in this clause of the normal morphology rule may be the same or different than the values used in morphology-related clauses of other rules. Normal morphology may be identified according to the wavelet transform or QRS width methods described above. If all of these clauses (steps 562–565) are met, the normal morphology rule is satisfied as indicated at step 568. If this rule is the highest priority rule satisfied, as will be determined at step 580 of FIG. 4, ventricular tachycardia therapy will be withheld. If any one of these clauses (steps 562 through 565) are not met, the normal morphology rule is not satisfied as indicated at step 569.

Additional rules, through "Rule N" at step 570 in FIG. 4, may also be applied, which preferably include at least the VF, fast VT and VT rules based on the Medtronic Model 7219 detection criteria as listed above. If no rules are satisfied, the algorithm returns to step 401 to await the next sensed ventricular event. If one or more rules are satisfied, as determined at decision step 575, the highest priority rule that is satisfied is selected at step 580 and used to classify the rhythm at step 590. As noted above, this classification may result in a withholding or delivery of ventricular cardioversion or defibrillation therapy.

Figure 8:
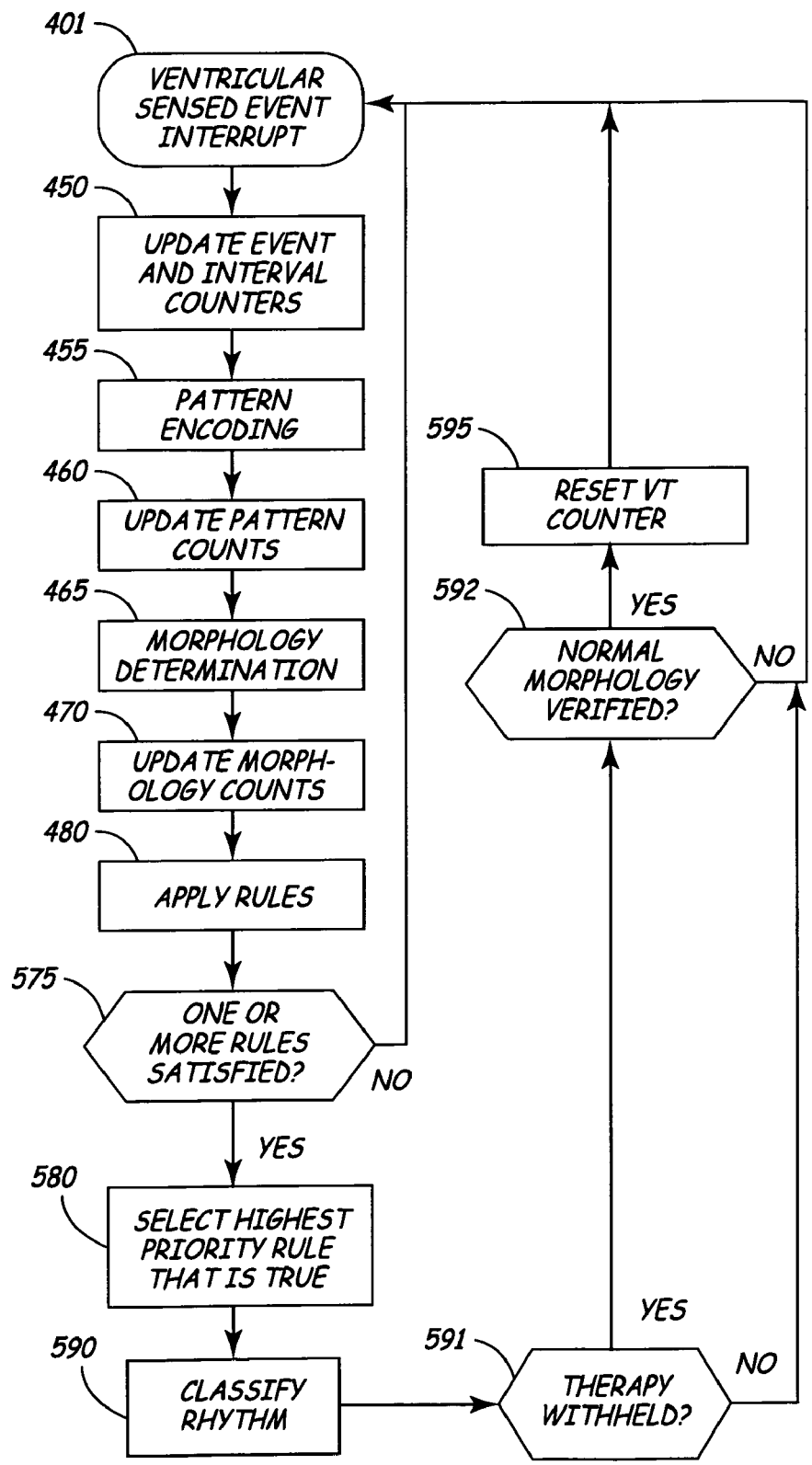
FIG. 8 is a flow chart depicting an alternative embodiment of the present invention.

FIG. 8 is a flow chart depicting an alternative embodiment of the present invention including the option of resetting a VT interval counter when a normal morphology criterion is met. In FIG. 8, identically numbered steps correspond to those shown in FIG. 4. Step 480 corresponds to steps 500 through 570 wherein the prioritized rules are applied. If the rhythm classification at step 590 results in no ventricular therapy being delivered, as determined at decision step 591, the arrhythmia detection algorithm may optionally reset the VT counter that tracks the number of intervals falling within the TDI at step 595 after first verifying that a VT rhythm is highly improbable at decision step 592 based on morphology analysis. In one embodiment, VT is highly improbable if a normal morphology has been verified for all or at least a predetermined number of beats during the last given number of beats. If this decision step 592 is affirmative, the VT counter may optionally be reset at step 595 prior to returning to step 401 to await the next ventricular sensed event. If the rhythm classification at step 590 resulted in a therapy delivery, or if normal morphology has not been verified at step 592, the VT counter reset step 595 is bypassed.

Figure 9:
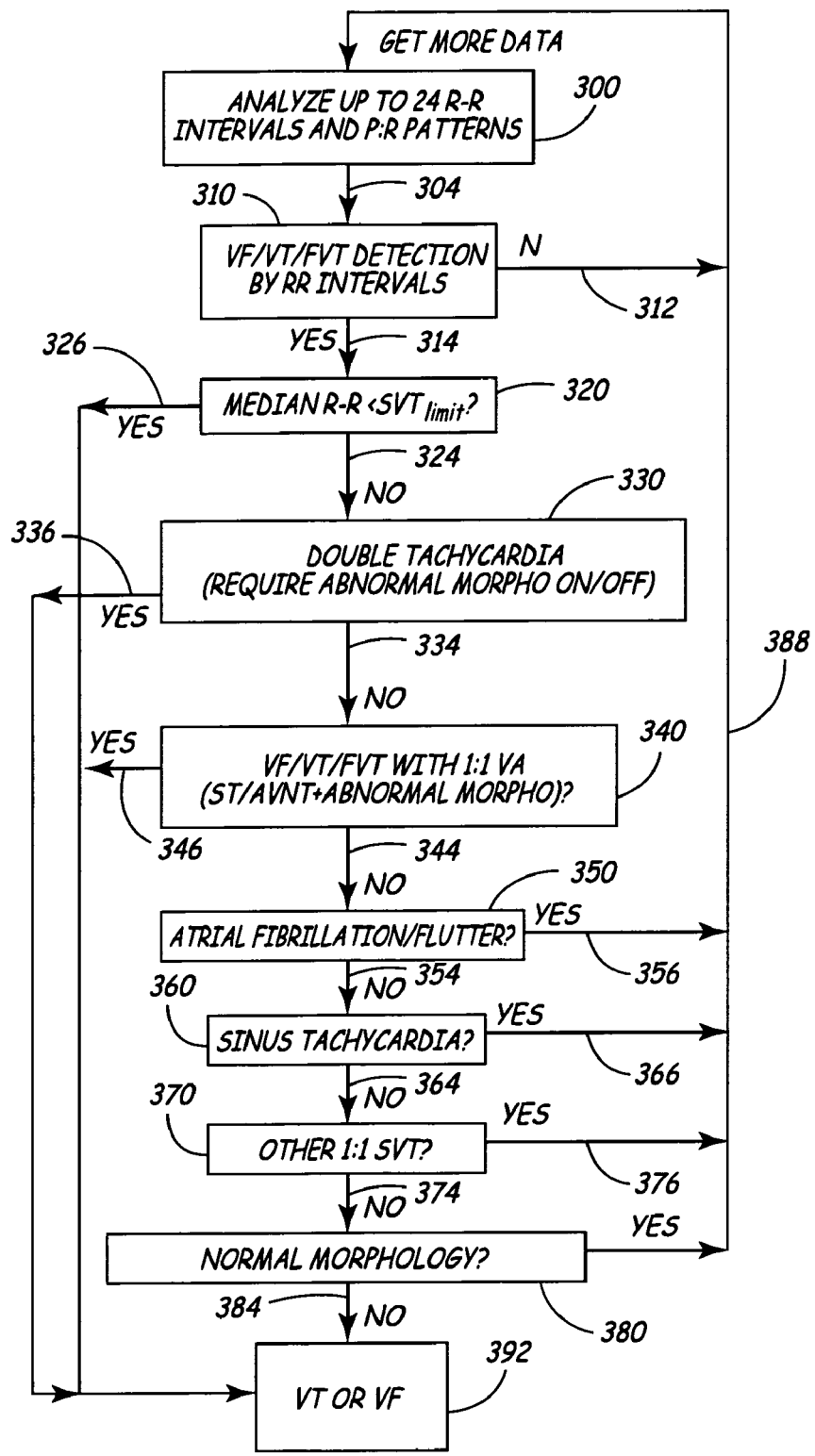
FIG. 9 is a flowchart illustrating detection of cardiac arrhythmias in an implantable medical device according to the present invention.

FIG. 9 is a flowchart illustrating detection of cardiac arrhythmias in an implantable medical device according to the present invention. As illustrated in FIG. 9, for each sensed ventricular event, information regarding atrial and ventricular pattern and rate is accumulated. For example, up to 24 R-R intervals and P:R patterns are analyzed, step 300, to determine the number of events that are ventricular fibrillation (VF) events, ventricular tachycardia (VT) events and fast ventricular tachycardia events (FVT). In step 310 the accumulated information is then analyzed to determine whether ventricular rate-only detection has been satisfied. If the event is not a VF/VT/FVT event, NO in step 310, the process returns to obtain information corresponding to the next ventricular event, step 300. However, if the event is a VF/VT/FVT event, YES in step 310, a determination is made as to whether a corresponding median RR interval is less than a predetermined supraventricular tachycardia limit (SVT$_{Limit}$), step 320. If the rhythm is detected as a VF/VT/FVT and a corresponding median RR interval is less than the predetermined supraventricular tachycardia limit, the rhythm is classified as a VT or VF event and appropriate therapy is applied, step 392.

On the other hand, if the rhythm is detected as a VF/VT/FVT and a corresponding median RR interval is greater than or equal to the predetermined supraventricular tachycardia limit, dual chamber interval only based criteria, such as PR dissociation and RR regularity, described above, are applied to determine whether the detected rhythm corresponds to a double tachycardia, step 330. According to the present invention, when determining whether the detected rhythm corresponds to a double tachycardia in step 330, the morphology corresponding to the rhythm is analyzed using EGM width or wavelet transform, described above, in addition to the dual chamber interval only double tachycardia criteria. If both the dual chamber interval only double tachycardia based criteria is met, i.e., the rhythm looks like atrial fibrillation but is PR dissociated with regular RR intervals, and QRS morphology is abnormal, the rhythm is classified as double tachycardia and VT/VF therapy is applied, step 392. If the dual chamber interval only double tachycardia based criteria are met and morphology is not abnormal, the algorithm advances to step 340.

In step 340, abnormal morphology is used to detect as VT with 1:1 retrograde, a rhythm that exhibits the PR pattern of a 1:1 SVT, such as sinus tachycardia or AVNRT. If the rhythm satisfies the criteria of dual chamber interval only rules for sinus tachycardia or other 1:1 SVT, which would lead to rejection by dual chamber interval rules alone, and the rhythm morphology is abnormal, the VF/FVT/VT with 1:1 VA rule is satisfied and VT/VF therapy is delivered, step 392. On the other hand, if either the rhythm satisfies the criteria of dual chamber interval only rules for sinus tachycardia or other 1:1 SVT and the morphology is not abnormal, or neither dual chamber interval only rules (for sinus tachycardia or other 1:1 SVT) is satisfied, then dual chamber interval only SVT rejection rules 350, 360 and 370 are applied.

If the dual chamber interval only SVT rejection rules 350, 360 and 370 are not satisfied, i.e., the rhythm is determined not to be atrial fibrillation, atrial flutter, sinus tachycardia, or another 1:1 SVT, a determination is made as to whether there is a normal morphology associated with the event, step 380. If the morphology associated with the event is abnormal, the rhythm is classified as a VT or VF and appropriate therapy is applied, step 392. However, if the morphology associated with the event is normal, therapy is withheld and the process returns to obtain information corresponding to the next ventricular event.

Figure 10:
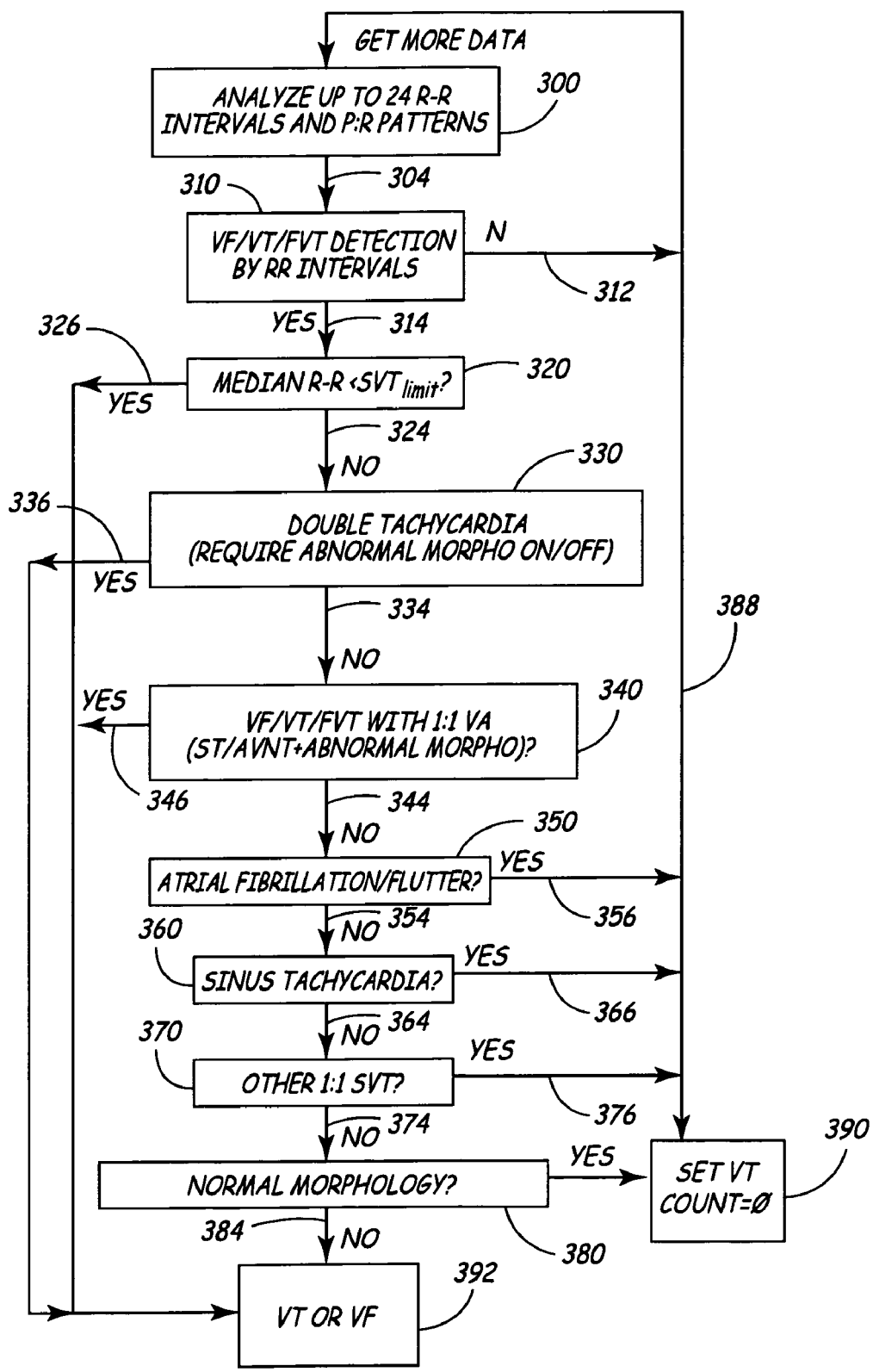
FIG. 10 is a flowchart illustrating detection of cardiac arrhythmias in an implantable medical device according to the present invention.

FIG. 10 is a flowchart illustrating detection of cardiac arrhythmias in an implantable medical device according to the present invention. Detection of cardiac arrhythmias according to the present invention illustrated in FIG. 10 differs from the detection process described above in reference to FIG. 9 only in that, according to an alternate embodiment of the present invention, a VT counter is reset to zero, Step 390, if it is determined that the event is not a VF/VT/FVT event in step 310, one of the dual chamber interval only SVT rejection rules 350, 360 and 370 is satisfied, or if the morphology associated with the event is normal in step 380.

Figure 11:
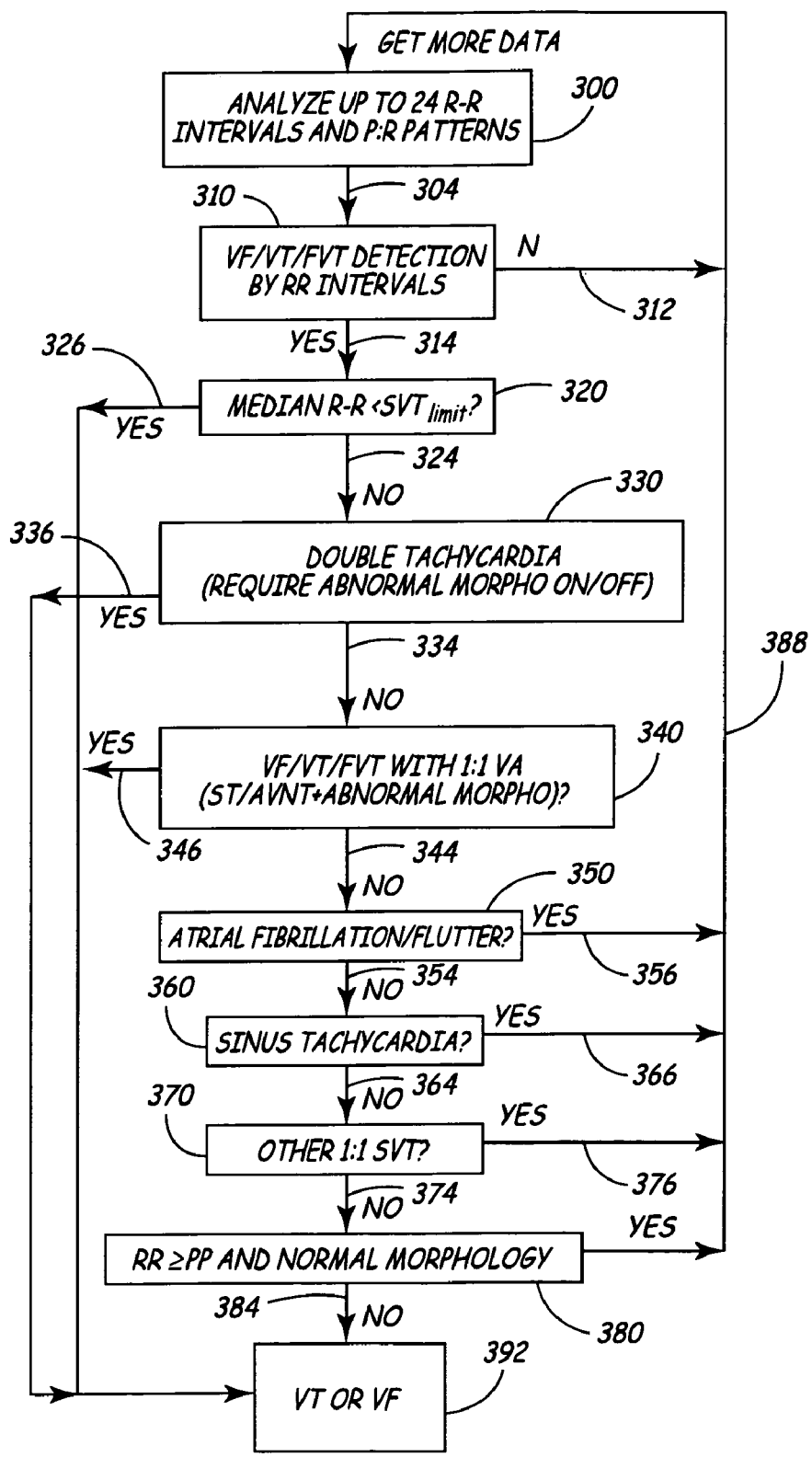
FIG. 11 is a flowchart illustrating detection of cardiac arrhythmias in an implantable medical device according to the present invention.

FIG. 11 is a flowchart illustrating detection of cardiac arrhythmias in an implantable medical device according to the present invention. Detection of cardiac arrhythmias according to the present invention illustrated in FIG. 11 differs from the detection process described above in reference to FIG. 9 only in that if the dual chamber interval only SVT rejection rules 350, 360 and 370 are not satisfied, i.e., the event is determined not to be atrial fibrillation, atrial flutter, sinus tachycardia, or another 1: SVT, a determination is made as to whether there is a normal morphology associated with the rhythm and whether an RR interval is greater than or equal to a PP interval of the event in step 380. If there is a normal morphology associated with the rhythm and the RR interval is greater than or equal to the PP interval associated with the event, YES in step 380, therapy is withheld and the process returns to obtain information corresponding to the next ventricular event, step 300. If the morphology associated with the rhythm is abnormal and the RR interval is less than the PP interval associated with the event, NO in step 380, VT/VF therapy is applied, step 392. In this way, in addition to the dual chamber interval only SVT rules, steps 350, 360 and 370 being satisfied, both the atrial rate must be greater than the ventricular rate and there must be a normal morphology associated with the event in order for therapy to be rejected, step 380.

It is understood that, according to the present invention, the morphology detection is performed in steps 330, 340 and 380 of FIGS. 9 and 10 is performed using either the EGM width or the wavelet transform associated with the event, as described above. It is also understood that what is meant above when describing the morphology of a rhythm as being "normal" or "abnormal" is that a "normal" morphology is one in which the rhythm has a morphology substantially equivalent to normal sinus rhythm, and an "abnormal" morphology is one in which the rhythm has a morphology that is not substantially equivalent to normal sinus rhythm.

It is also understood that the device may be programmed so that each of rules 330, 3340 and 380 may be programmed on or off, in any combination desired.

In the flow chart of FIG. 9, step 300 analyzes up to 24 R-R intervals and P:R patterns. Then path 304 leads to step 310 in which there is a determination of VF/VT/FVT detection by RR intervals. If no detection, then path 312 routes to VT counter reset to zero step 390. If yes at step 310, then path 314 leads to step 320 at which logic determines whether the median R-R is less than $SVT_{limits}$. If yes, then path 326 leads to VT/VF therapy 392. If step 320 answer is no, then path 324 leads to double tachycardia step 330. At this step if double tachycardia (i.e. dual chamber tachycardia) exists and there are either 6, 7, or 8 wide beats, then path 336 leads to VT/VF therapy 392. If step 330 leads to a no determination, then path 334 routes to step 340. At this step, it is determined whether there exists a VF, VT, or FVT along with a 1:1 VA, and if there are either 6, 7, or 8 wide beats, then path 346 leads, once again, to VT or VF therapy 392. If prior step 340 is a no determination, then path 444 leads to step 350. Atrial fibrillation/flutter step 350 determines the existence of either activity and if such is detected then path 356 leads to VT counter reset to zero step 390. Accordingly, if step 350 is negative, then path 354 leads to a sinus tachycardia determination at step 360. If yes, then path 366 leads to the VT counter reset to zero step 390, and if no then path 364 leads to step 370. At this step 370, there is determined whether there may be other 1:1 SVT present, and if yes then path 376 leads to VT counter reset to zero step 390. If the determination in step 370 is negative, then path 374 leads to step 380, at which it is determined whether the rhythm has greater than x of 8 narrow beats, with x preferably being the value of 6. If yes, then path 382 leads to VT counter reset to zero step 390. If no, then path 384 leads to VT or VF therapy 392. This algorithm is thus designed to increase the sensitivity and specificity under the conditions prescribed.

The design of the dual chamber wavelet detection algorithm is a combination of PR Logic and the wavelet template matching morphology algorithms. The design philosophy for the feature is to apply the wavelet algorithm where PR Logic has difficulty discriminating, for example, to improve the specificity of existing (PR Logic) algorithms. These improvements relate to detection of sinus tachycardia/atrial tachycardia with long PR or intermittent far field r-wave (FFRW); rapidly conducted AF and other 1:1 rhythms (nearly simultaneous P and R).

The combined algorithm, which is also referred to herein as the dual chamber wavelet detection algorithm, is designed to address problematic arrhythmias by applying a single chamber wavelet algorithm when the intervals resemble one of the problem rhythms. In these cases, the wavelet algorithm is able to overrule the PR Logic decision in appropriate circumstances.

Referring to FIG. 11, blocks or steps 330, 340 and 380 relate to the wavelet algorithm rules and the remaining steps relate to the previous PR Logic related rules. It is noted that blocks 330, 340, and 380 may be separately programmed as ON/OFF in firmware. This programmable feature is also true for steps 330, 340, and 380 of FIG. 9.

In FIG. 11, the PR Logic VF+SVT Double Tachycardia Rule shown in step 330, was created to detect VF in the presence of AF. When these double tachycardias occur, the atrial rate can be faster than the ventricular rate such that the AF Evidence counter may be satisfied. Interval-only detection provides little help in discriminating AF from VF+AF: both rhythms being typically irregular in the ventricle. The criterion that is used in PR Logic is AV Dissociation: when satisfied the rhythm is VF+AF; otherwise the rhythm is AF. When AF is conducted rapidly to the ventricle it is common for conduction through the AV Node to become irregular which creates AV Dissociation and results in inappropriate detection as double tachycardia. The new Double Tachycardia (VF+SVT) rule requires morphology to differ from sinus in order to detect in addition to the PR Logic criteria. The morphology criterion can be hidden programmed OFF, but is nominally ON when both AF/AT rejection and Wavelet rejection are ON. Thus, the rule description of step 330 includes:

Current PR Logic VF+SVT (FVT via VF+SVT): (VF count, SVT limit, AF evidence, AV dissoc)

AND

At least N of last 8 beats abnormal (N is "hidden" programmable 1–8, nominal 6 as for single chamber wavelet)

AND

Current RR interval in the tachy zone.

In another embodiment, the PR Logic VT+SVT Double Tachycardia Rule was created to detect VT in the presence of AF. When these double tachycardias occur, the atrial rate can be faster than the ventricular rate such that the AF Evidence counter may be satisfied. Interval-only detection in the VT zone provides better discrimination than in the VF zone because of differences in ventricular interval regularity between AF and VT+AF. However, there are still instances where the VT+AF rule detects inappropriately. The new Double Tachycardia (VT+SVT) rule requires morphology to differ from sinus in order to detect in addition to the PR Logic criteria. As noted above, the morphology criterion can be hidden programmed OFF, but is nominally ON when both AF/AT rejection and Wavelet rejection are ON. The rule description of this embodiment of step 330 includes:

Current PR Logic VT+SVT: (VT count, SVT limit, AF evidence, AV dissoc, RR regularity)

AND

At least N of last 8 beats abnormal (N is "hidden" programmable 1–8, BUT is same as for VF+SVT)

AND

Current RR interval in tachy zone

Step 340 depicts the logic step having the rule to address the problem of VT with 1:1 retrograde conduction that cannot be perfectly discriminated from sinus tachycardia or AVNRT on the basis of intervals alone. This rule serves much the same purpose as the other double tachycardia rules: interval data alone is ambiguous regarding whether the rhythm is VT or SVT; overrule the SVT rule (in this case sinus tach or Other 1:1 rules) when there is sufficient evidence that the rhythm is truly VT. The VT with 1:1 VA rule description includes:

Any number of intervals for detection (NID) criteria met (VF NID, VT NID, CC NID)
AND
New ST or Other 1:1 SVT rule satisfied (Median RR>=SVT limit)
AND
At least N of last 8 beats abnormal (N is "hidden" programmable 1–8, BUT is same as VF+SVT)
AND
Current RR interval in tachy zone.

Step 380 is for non-specific SVT rejection having normal morphology and at least 1:1 A:V. This rule is a modification of the morphology rejection rule. Note that this is the only rejection rule among the new or modified DC Wavelet rules in this Figure. When both PR Logic and wavelet are enabled, this rule will only be tested after PR Logic has failed to identify a specific SVT (AF/AT, ST or Other 1:1). Thus, PR Logic alone would detect VT/VF. The combination of PR Logic and wavelet will allow non-specific SVTs (or specific SVTs which have fooled PR Logic) to be rejected on the basis of morphology, but only when there is enough evidence to overrule the PR Logic decision to detect. The non-specific SVT Rejection rule includes:

SVTmin≦RR Median<TDI
AND
RR Median>=0.9375*PP Median
AND

At least M of last 8 beats NORMAL (M is "hidden" programmable from 1–8, nominal 3. This parameter is different than that used for the detection rules such as VF+SVT.)
When the above conditions are met:
Fire the "Normal Morphology" SVT rule, set sticky count, withhold VT detection (NO VT counter reset)

Note that the second criterion should be read as apply morphology only when RR rate is not faster than PP rate. When PP rate is greater than or equal to RR rate, apply morphology. The 0.9375 factor handles the case of a 1:1 rhythm such as AVNRT in which the medians may not be exactly the same on every beat, but RR rate is clearly not greater than PP rate.

Note that the third criterion uses the count of NORMAL beats instead of ABNORMAL beats because this is a rejection criterion instead of a detection criterion. Nominally this should be set at 3, as for the single chamber wavelet algorithm.

Thus, a method and apparatus for classifying a heart rhythm according to an algorithm that combines dual-chamber interval analysis and EGM morphology analysis has been described. While detailed descriptions of preferred embodiments have been described herein, alternative embodiments are conceivable which include rule sets for identifying other types of rhythms or contain clauses other than the specific clauses described herein but do include morphology-related and rate or interval-related clauses in a prioritized set of rules for classifying a heart rhythm. The detailed embodiments presented herein, therefore, are intended to be exemplary, not limiting, with regard to the following claims.

The invention claimed is:

1. An implantable medical device, comprising:
means for sensing cardiac events;
means for applying interval only logic steps to determine cardiac rhythms in response to the sensed cardiac events;
means for combining morphology based considerations of the cardiac rhythms with the interval only logic steps to achieve improved specificity in arrhythmia detection of the apparatus without loss of sensitivity;
means for generating a VT (ventricular tachycardia) count; and
means for delivering therapy in response to the means for combining, wherein, in response to interval only logic steps corresponding to SVT (supraventricular tachycardia) rejection not being satisfied, the combining means determines whether the cardiac rhythms have a morphology that corresponds to sinus rhythm, therapy is delivered by the delivery means in response to the cardiac rhythms having a morphology that does not correspond to sinus rhythm and therapy is withheld by the delivery means in response to the cardiac rhythms having a morphology that corresponds to sinus rhythm, and wherein the generating means resets the VT count in response to the therapy being withheld by the delivery means in response to the cardiac rhythms having a morphology that corresponds to sinus rhythm.

2. The implantable medical device of claim 1, wherein the morphology based considerations correspond to one of an EGM width corresponding to the cardiac rhythms and a wavelet transform corresponding to the cardiac rhythms.

3. The implantable medical device of claim 1, wherein the combining means combines interval only logic steps for determining whether the cardiac rhythms correspond to a double tachycardia and morphology of the cardiac rhythms to determine whether the cardiac rhythms correspond to a double tachycardia, and wherein the cardiac rhythms are determined to correspond to double tachycardia in response to the interval only logic steps for determining whether the cardiac rhythms correspond to a double tachycardia being satisfied and the cardiac rhythms having a morphology that does not correspond to sinus rhythm.

4. The implantable medical device of claim 1, wherein the combining means combines interval only logic steps for determining whether the cardiac rhythms correspond to a double tachycardia and morphology of the cardiac rhythms to determine whether the cardiac rhythms correspond to a double tachycardia, and wherein the cardiac rhythms are determined to not correspond to double tachycardia in response to one of the interval only logic steps for determining whether the cardiac rhythms correspond to a double tachycardia not being satisfied and the cardiac rhythms having a morphology that corresponds to sinus rhythm.

5. The implantable medical device of claim 1, wherein the combining means combines interval only logic steps for sinus tachycardia or other 1:1 SVT (supraventricular tachycardia) and morphology of the cardiac rhythms to determine whether VF/FVT/VT (ventricular fibrillation/fast ventricular tachycardia/ventricular tachycardia) with 1:1 VA (ventricular atrial) is satisfied, and wherein VF/FVT/VT with 1:1 VA is satisfied in response to cardiac rhythms satisfying the interval only logic steps for sinus tachycardia or other 1:1 SVT and the cardiac rhythms having a morphology that does not correspond to sinus rhythm.

6. The implantable medical device of claim 1, wherein the combining means combines interval only logic steps for sinus tachycardia or other 1:1 SVT and morphology of the cardiac rhythms to determine whether VF/FVT/VT with 1:1 VA is satisfied, and wherein VF/FVT/VT with 1:1 VA is not satisfied in response to one of the cardiac rhythms satisfying the interval only logic steps for sinus tachycardia or other 1:1 SVT and the cardiac rhythms having a morphology that corresponds to sinus rhythm and the cardiac rhythms not satisfying the interval only logic steps for one of sinus tachycardia and other 1:1 SVT.

7. The implantable medical device of claim 1, wherein in response to the interval only logic steps corresponding to SVT rejection not being satisfied, the combining means determines whether the cardiac rhythms have a morphology that corresponds to sinus rhythm and whether an RR interval is greater than or equal to a PP interval, and wherein therapy is delivered by the delivery means in response to the cardiac rhythms having a morphology that does not correspond to sinus rhythm and the RR interval is not greater than or equal to the PP interval.

8. The implantable medical device of claim 7, wherein therapy is withheld by the delivery means in response to the cardiac rhythms having a morphology that corresponds to sinus rhythm and the RR interval being greater than or equal to the PP interval.

9. The implantable medical device of claim 8, wherein the generating means resets the VT count in response to the therapy being withheld by the delivery means in response to the cardiac rhythms having a morphology that corresponds to sinus rhythm and the RR interval being greater than or equal to the PP interval.

10. The implantable medical device of claim 1, wherein combining means determines that morphology of the cardiac rhythms does not corresponds to sinus rhythm in response to a first predetermined number of beats out of a second predetermined number of beats being wide beats.

11. An implantable medical device, comprising:
means for sensing cardiac events;
means for applying interval only logic steps to determine cardiac rhythms in response to the sensed cardiac events;
means for combining morphology based considerations of the cardiac rhythms with the interval only logic steps to achieve improved specificity in arrhythmia detection of the apparatus without loss of sensitivity; and means for delivering therapy in response to the means for combining, wherein combining means determines that morphology of the cardiac rhythms does not corresponds to sinus rhythm in response to a first predetermined number of beats out of a second predetermined number of beats being wide beats and the first predetermined number is one of 6, 7 and 8 and the second predetermined number is eight.

12. An implantable medical device, comprising:
means for sensing cardiac events;
means for applying interval only logic steps to determine cardiac rhythms in response to the sensed cardiac events;
means for combining interval only logic steps for determining whether the cardiac rhythms correspond to a double tachycardia and morphology of the cardiac rhythms to determine whether the cardiac rhythms correspond to a double tachycardia, combining interval only logic steps for sinus tachycardia or other 1:1 SVT (supraventricular tachycardia) and morphology of the cardiac rhythms to determine whether VF/FVT/VT (ventricular fibrillation/fast ventricular tachycardia/ ventricular tachycardia) with 1:1 VA (ventricular atrial) is satisfied, and determining whether the cardiac rhythms have a morphology that corresponds to sinus rhythm and whether an RR interval is greater than or equal to a PP interval; and
means for delivering therapy in response to the means for combining, wherein the morphology based considerations correspond to one of an EGM width corresponding to the cardiac rhythms and a wavelet transform corresponding to the cardiac rhythms, combining means determines that morphology of the cardiac rhythms does not corresponds to sinus rhythm in response to a first predetermined number of beats out of a second predetermined number of beats being wide beats, and the first predetermined number is one of 6, 7 and 8 and the second predetermined number is eight.

13. The implantable medical device of claim 12, wherein the cardiac rhythms are determined to correspond to double tachycardia in response to the interval only logic steps for determining whether the cardiac rhythms correspond to a double tachycardia being satisfied and the cardiac rhythms having a morphology that does not correspond to sinus rhythm, VF/FVT/VT with 1:1 VA is satisfied in response to cardiac rhythms satisfying the interval only logic steps for sinus tachycardia or other 1:1 SVT and the cardiac rhythms having a morphology that does not correspond to sinus rhythm, and therapy is delivered by the delivery means in response to the cardiac rhythms having a morphology that does not correspond to sinus rhythm and the RR interval is not greater than or equal to the PP interval.

14. The implantable medical device of claim 13, wherein the cardiac rhythms are determined to not correspond to double tachycardia in response to one of the interval only logic steps for determining whether the cardiac rhythms correspond to a double tachycardia not being satisfied and the cardiac rhythms having a morphology that corresponds to sinus rhythm, VF/FVT/VT with 1:1 VA is not satisfied in response to one of the cardiac rhythms satisfying the interval only logic steps for sinus tachycardia or other 1:1 SVT and the cardiac rhythms having a morphology that corresponds to sinus rhythm and the cardiac rhythms not satisfying the interval only logic steps for one of sinus tachycardia and other 1:1 SVT, and therapy is withheld by the delivery means in response to the cardiac rhythms having a morphology that corresponds to sinus rhythm and the RR interval being greater than or equal to the PP interval.

15. The implantable medical device of claim 14, wherein the cardiac rhythms are determined to correspond to double tachycardia in response to the interval only logic steps for determining whether the cardiac rhythms correspond to a double tachycardia being satisfied and the cardiac rhythms having a morphology that does not correspond to sinus rhythm, and VF/FVT/VT with 1:1 VA is satisfied in response to cardiac rhythms satisfying the interval only logic steps for sinus tachycardia or other 1:1 SVT and the cardiac rhythms having a morphology that does not correspond to sinus rhythm.

16. The implantable medical device of claim 15, wherein the cardiac rhythms are determined to not correspond to double tachycardia in response to one of the interval only logic steps for determining whether the cardiac rhythms correspond to a double tachycardia not being satisfied and the cardiac rhythms having a morphology that corresponds to sinus rhythm, VF/FVT/VT with 1:1 VA is not satisfied in response to one of the cardiac rhythms satisfying the interval only logic steps for sinus tachycardia or other 1:1 SVT and the cardiac rhythms having a morphology that corresponds to sinus rhythm and the cardiac rhythms not satisfying the interval only logic steps for one of sinus tachycardia and other 1:1 SVT, and, in response to interval only logic steps corresponding to SVT rejection not being satisfied, therapy is delivered by the delivery means in response to the cardiac rhythms having a morphology that does not correspond to sinus rhythm.

17. The implantable medical device of claim 16, wherein, in response to interval only logic steps corresponding to SVT rejection not being satisfied, therapy is withheld by the delivery means in response to the cardiac rhythms having a morphology that corresponds to sinus rhythm.

18. The implantable medical device of claim 17, further comprising means for generating a VT count, wherein the generating means resets the VT count in response to the therapy being withheld by the delivery means in response to the cardiac rhythms having a morphology that corresponds to sinus rhythm and the RR interval being greater than or equal to The PP interval.

* * * * *